(12) United States Patent
Rasooly et al.

(10) Patent No.: US 11,185,603 B2
(45) Date of Patent: Nov. 30, 2021

(54) CATHETER CONNECTION SYSTEM FOR ULTRAVIOLET LIGHT DISINFECTION

(71) Applicant: PURACATH MEDICAL, INC., San Francisco, CA (US)

(72) Inventors: Julia A. Rasooly, San Francisco, CA (US); John E. Ashley, Danville, CA (US)

(73) Assignee: PURACATH MEDICAL, INC., San Francisco, CA (US)

( * ) Notice: Subject to any disclaimer, the term of this patent is extended or adjusted under 35 U.S.C. 154(b) by 63 days.

(21) Appl. No.: 16/316,930

(22) PCT Filed: Jul. 11, 2017

(86) PCT No.: PCT/US2017/041544
§ 371 (c)(1),
(2) Date: Jan. 10, 2019

(87) PCT Pub. No.: WO2018/013572
PCT Pub. Date: Jan. 18, 2018

(65) Prior Publication Data
US 2019/0224352 A1   Jul. 25, 2019

Related U.S. Application Data

(60) Provisional application No. 62/360,927, filed on Jul. 11, 2016.

(51) Int. Cl.
*A61L 2/10* (2006.01)
*A61M 1/28* (2006.01)
(Continued)

(52) U.S. Cl.
CPC .................. *A61L 2/10* (2013.01); *A61L 2/00* (2013.01); *A61M 1/285* (2013.01);
(Continued)

(58) Field of Classification Search
CPC .. A61L 2/00; A61L 2/0047; A61L 2/10; A61L 2202/14; A61L 2202/24;
(Continued)

(56) References Cited

U.S. PATENT DOCUMENTS 3,986,508 A * 10/1976 Barrington ................ A61L 2/00
604/411
4,412,834 A * 11/1983 Kulin ................... A61M 1/1674
604/29
(Continued)

FOREIGN PATENT DOCUMENTS

CN          1420792 A      5/2003
CN        103619372 A      3/2014
(Continued)

OTHER PUBLICATIONS

European Search Opinion, App. No. EP16765846.7, dated Oct. 31, 2018, 1 Page.
(Continued)

*Primary Examiner* — Timothy C Cleveland
(74) *Attorney, Agent, or Firm* — Vorys, Sater, Seymour & Pease

(57) ABSTRACT

Systems and methods of disinfection of catheter connections are provided. A transfer catheter connector can include a UV-transparent window at its distal end and a seal proximal to the window. A solution set connector can be inserted inside a portion of the transfer catheter connector to connect a solution set and transfer catheter. The solution set connector comprises a lumen covered by a leading membrane surface; and a sealing surface configured to sealingly engage the window surface. The connectors can be connected in a disinfection position configuration in which flow is not permitted between the catheters and the connectors are irradiated with UV light. After disinfection, the connectors are advanced to a flow position in which the piercing (Continued)

member pierces the membrane surface, enabling flow between the catheters. The system comprises clips that prevent advancement to the flow position without interference by the disinfection unit or by a user.

15 Claims, 35 Drawing Sheets

(51) Int. Cl.
  *A61L 2/00* (2006.01)
  *A61M 39/02* (2006.01)
(52) U.S. Cl.
  CPC ....... *A61L 2202/14* (2013.01); *A61L 2202/24* (2013.01); *A61M 2039/0285* (2013.01)
(58) Field of Classification Search
  CPC ...... A61M 1/285; A61M 39/14; A61M 39/16; A61M 39/165; A61M 39/167; A61M 39/221; A61M 39/26; A61M 2039/0285; A61M 2039/1066; A61M 2039/1072
  See application file for complete search history.

(56) References Cited

U.S. PATENT DOCUMENTS

| | | | |
|---|---|---|---|
| 4,457,749 | A | 7/1984 | Bellotti et al. |
| 4,457,794 | A | 7/1984 | Kotera et al. |
| 4,473,369 | A | 9/1984 | Lueders et al. |
| 4,620,845 | A | 11/1986 | Popovich et al. |
| 4,882,496 | A | 11/1989 | Bellotti et al. |
| 4,950,260 | A | 8/1990 | Bonaldo |
| 6,461,568 | B1 | 10/2002 | Eckhardt |
| 7,834,328 | B2 | 11/2010 | Redmond et al. |
| 2005/0013729 | A1 | 1/2005 | Brown-Skrobot et al. |
| 2006/0202146 | A1 | 9/2006 | Doyle |
| 2007/0274879 | A1 | 11/2007 | Millikin |
| 2009/0001720 | A1 | 1/2009 | Cheon et al. |
| 2009/0012451 | A1 | 1/2009 | Sobue et al. |
| 2009/0012459 | A1 | 1/2009 | Sobue et al. |
| 2011/0125013 | A1 | 5/2011 | Neer |
| 2012/0116294 | A1 | 5/2012 | Boenig et al. |
| 2012/0206992 | A1 | 8/2012 | Stewart |
| 2012/0296151 | A1 | 11/2012 | Curtis et al. |
| 2014/0334974 | A1 | 11/2014 | Rasooly et al. |
| 2015/0352348 | A1 | 12/2015 | Murphy-Chutorian et al. |
| 2016/0082138 | A1 | 3/2016 | Kermode et al. |
| 2016/0271312 | A1 | 9/2016 | Lance et al. |
| 2019/0224352 | A1 | 7/2019 | Rasooly et al. |

FOREIGN PATENT DOCUMENTS

| | | | | |
|---|---|---|---|---|
| CN | 110049790 | A | 7/2019 | |
| EP | 0070087 | B1 | 1/1986 | |
| EP | 3270979 | A1 | 1/2018 | |
| WO | 3302060 | A1 | 6/1983 | |
| WO | WO-8302060 | A1 * | 6/1983 | ............ A61M 39/16 |
| WO | 2016044613 | A1 | 3/2016 | |
| WO | 2016149645 | A1 | 9/2016 | |
| WO | 2018013572 | A1 | 1/2018 | |

OTHER PUBLICATIONS

First Office Action, Chinese App. No. 201780052621.6, dated Apr. 2, 2021, 16 Pages.
First Office Action, Chinese Application No. 201680028643.4, dated Feb. 13, 2020, 19 Pages.
International Search Report, App. No. PCT/US2016/023207, dated Jun. 16, 2016, 2 Pages.
Lance, et al., U.S. No. U.S. Appl. No. 62/135,080, filed Mar. 18, 2015, 22 Pages.
Lance, et al., U.S. No. U.S. Appl. No. 62/238,644, filed Oct. 7, 2015, 38 Pages.
Non-Final Office Action, U.S. Appl. No. 15/074,854, dated Jun. 16, 2020, 24 Pages.
Notice of Allowance, U.S. Appl. No. 15/074,854, dated Nov. 18, 2020, 14 Pages.
Search Report, Chinese App. No. 201780052616, dated Apr. 2, 2021, XX Pages.
Written Opinion of the International Searching Authority, App. No. PCT/US2016/023207, dated Jun. 16, 2016, 12 Pages.

* cited by examiner

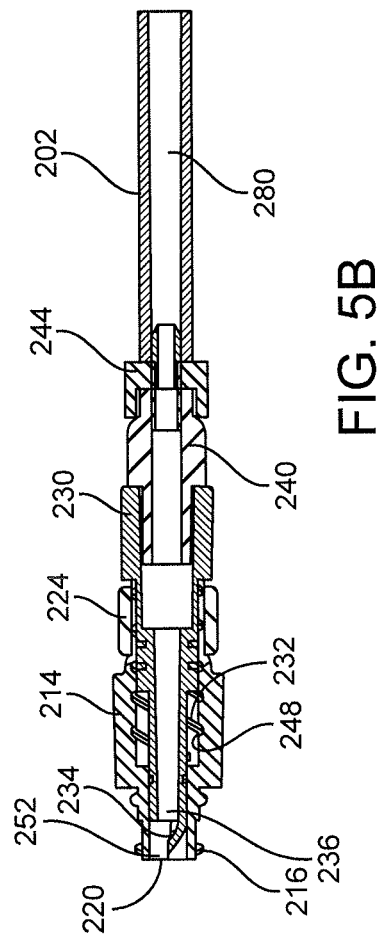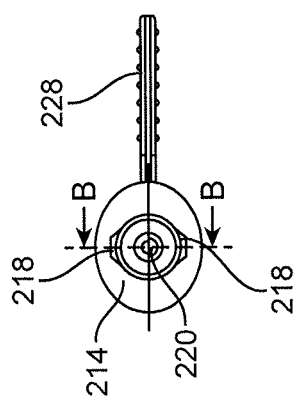

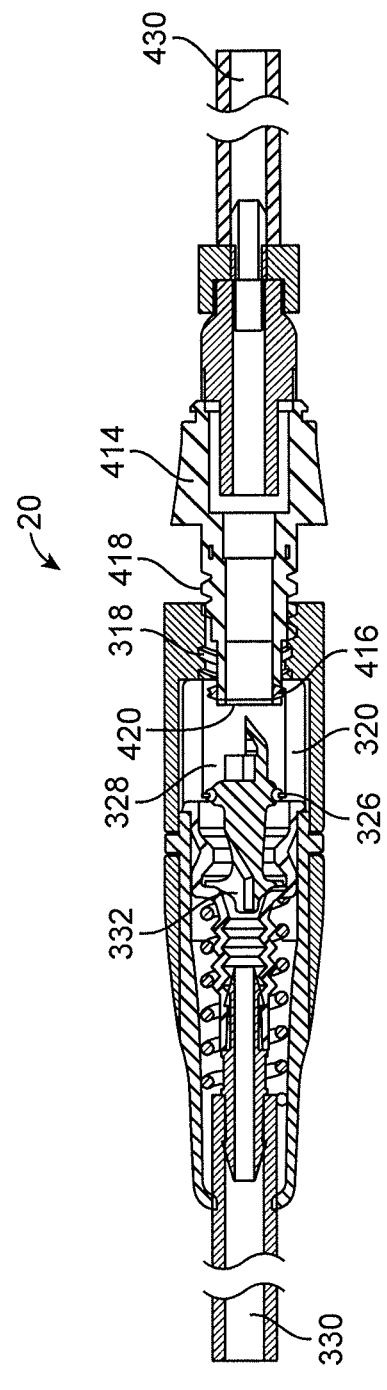
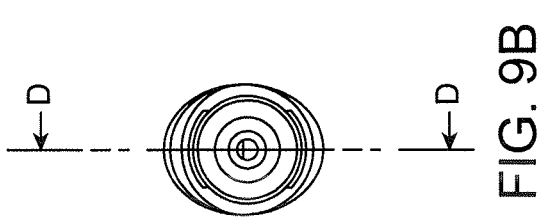
FIG. 9C
FIG. 9B

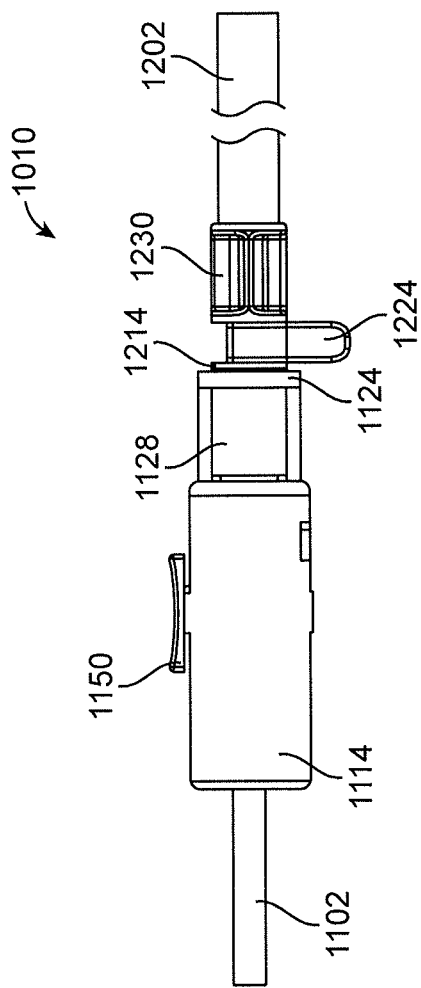
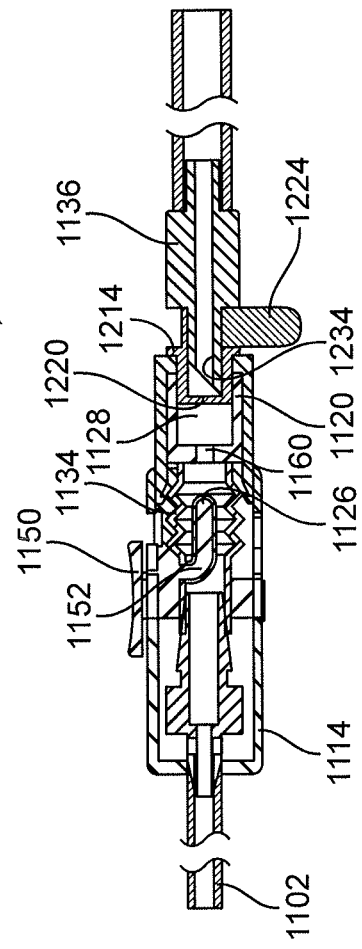
FIG. 10A
FIG. 10B
FIG. 10C

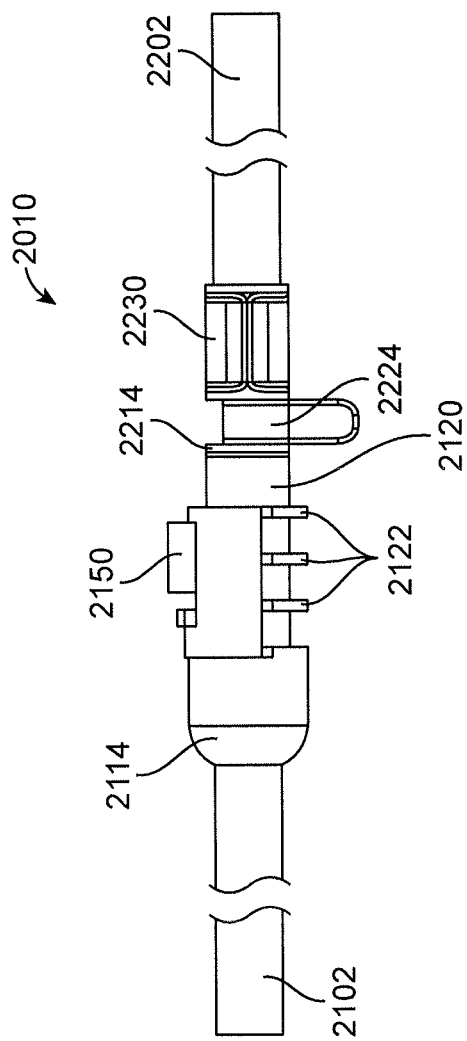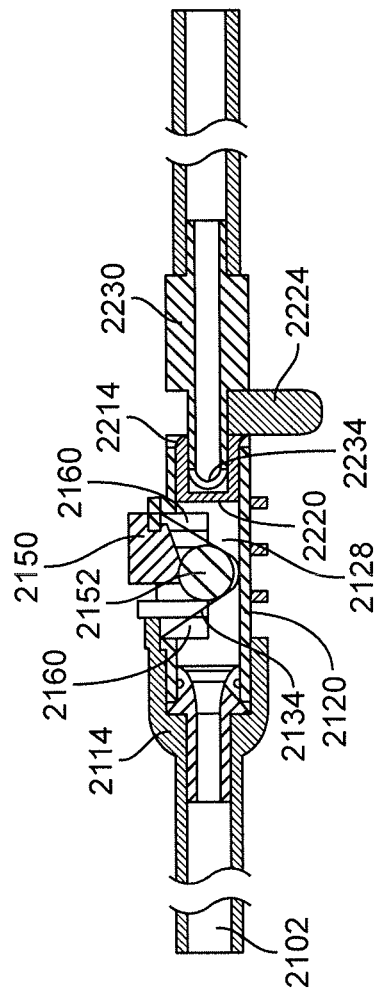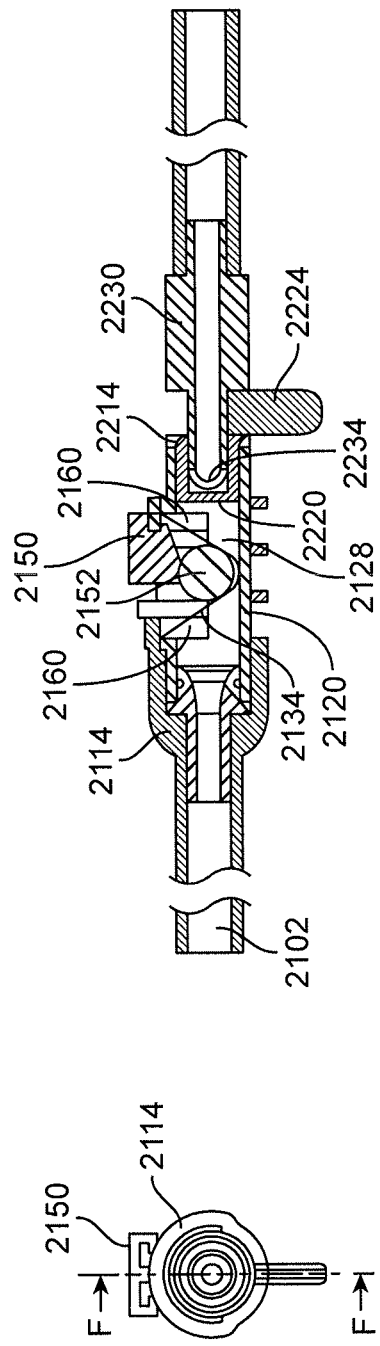
FIG. 11A
FIG. 11B
FIG. 11C

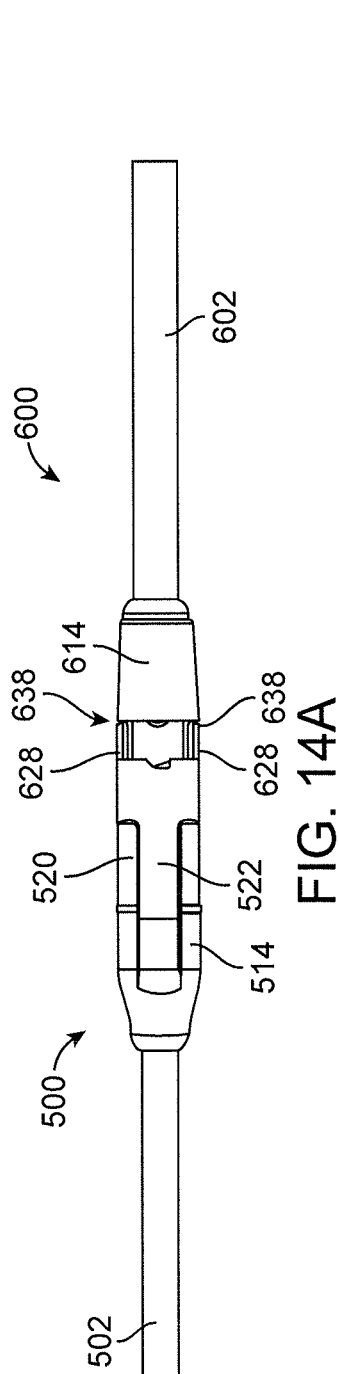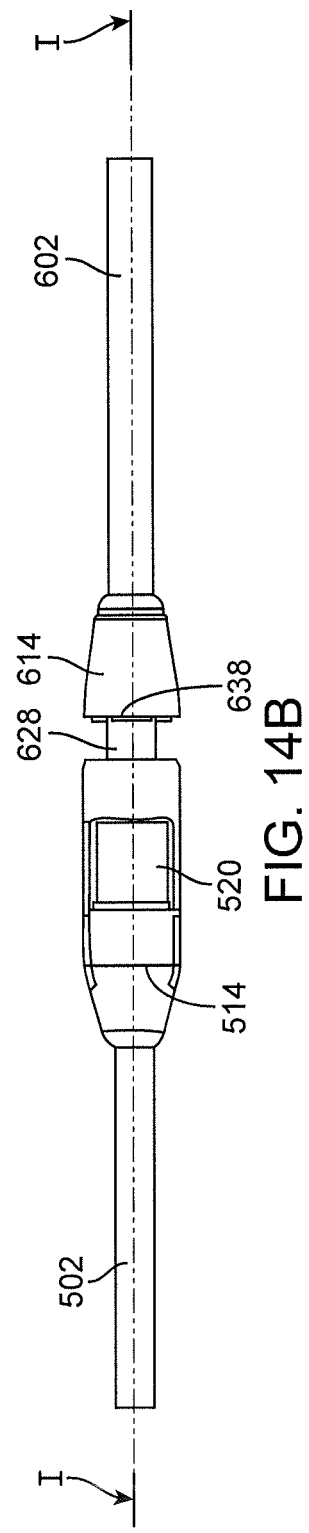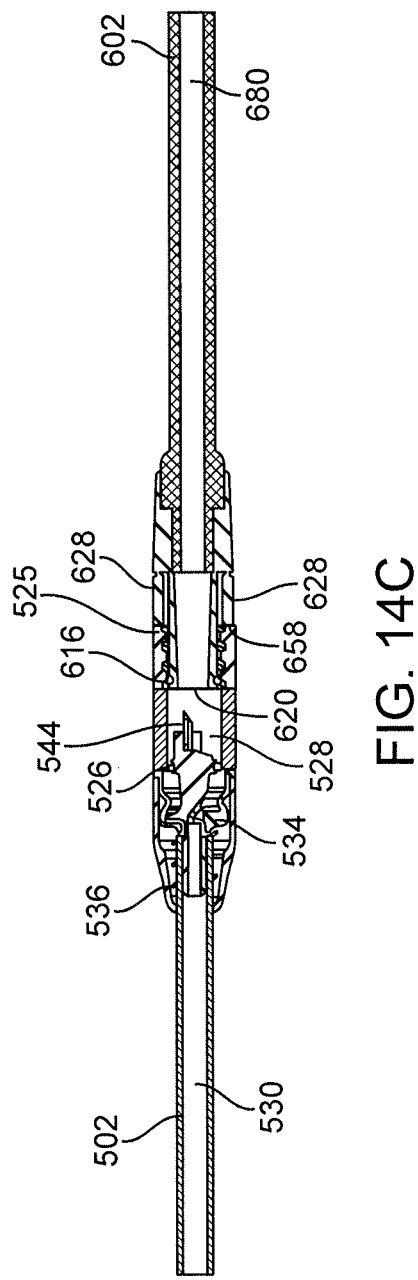

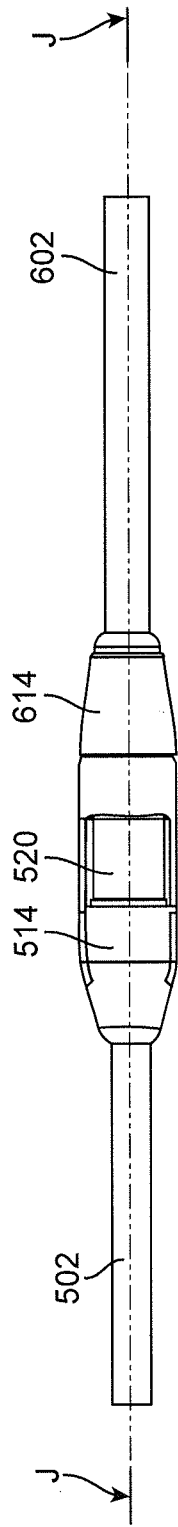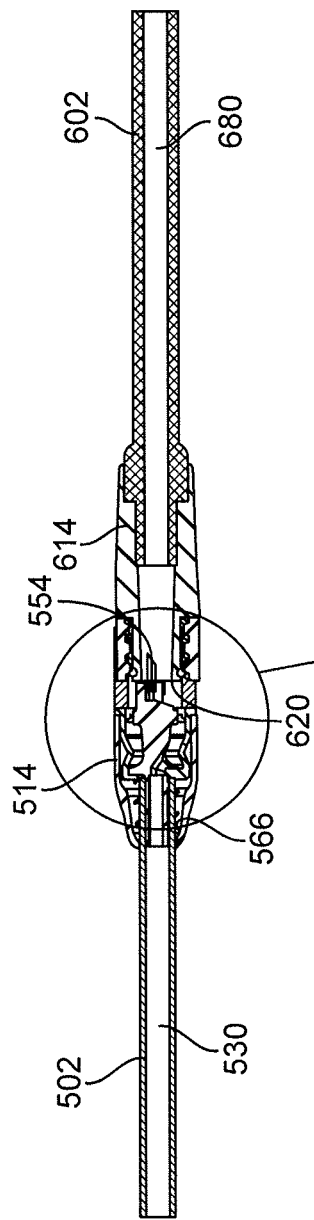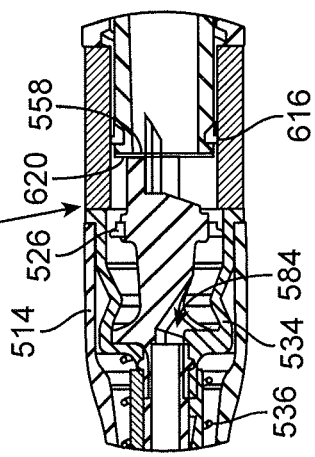

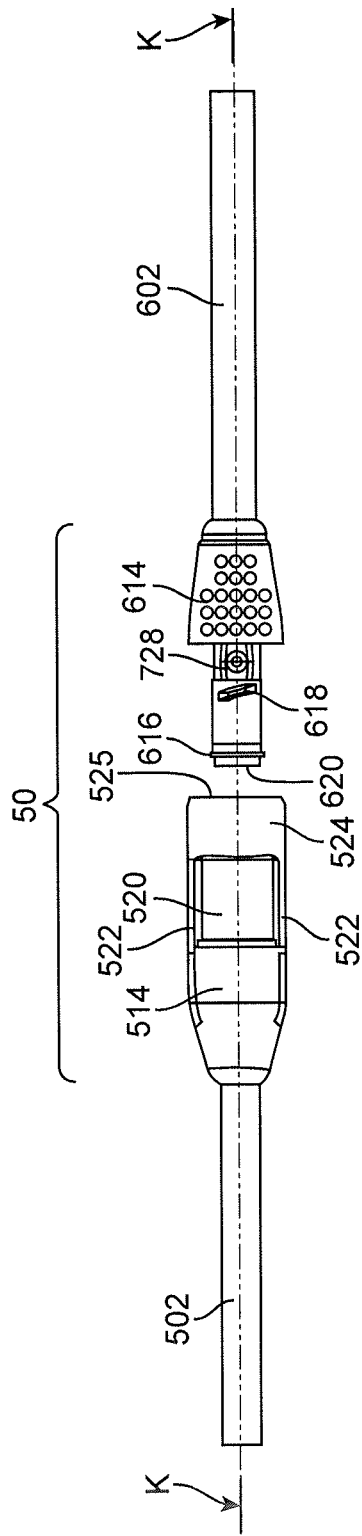
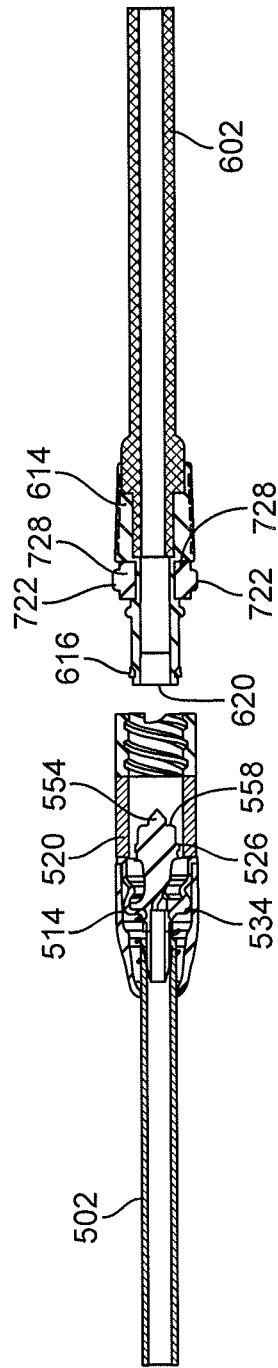
FIG. 16A
FIG. 16B

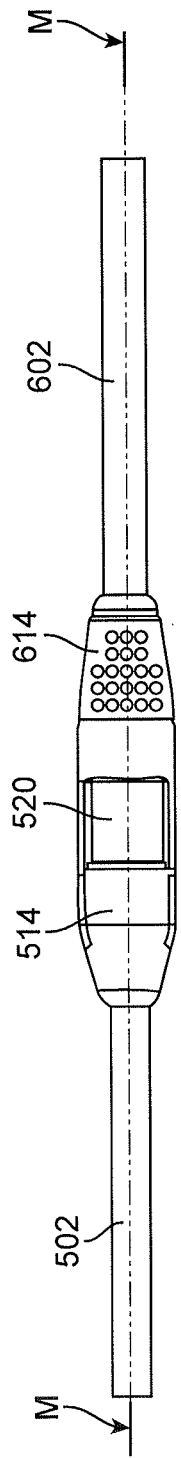
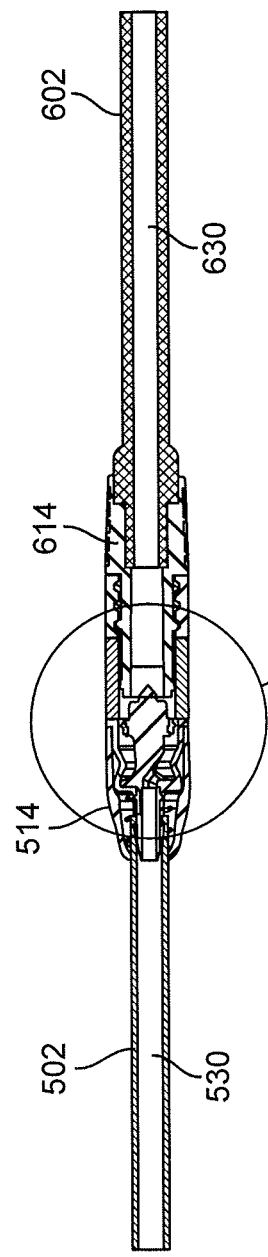
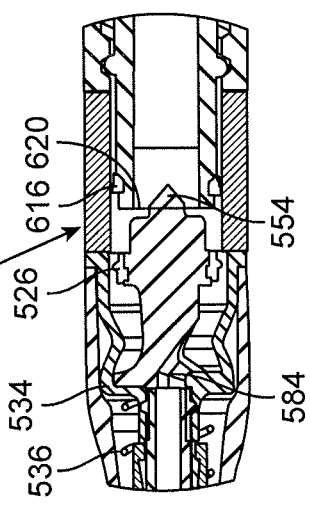
FIG. 18A
FIG. 18B
FIG. 18C

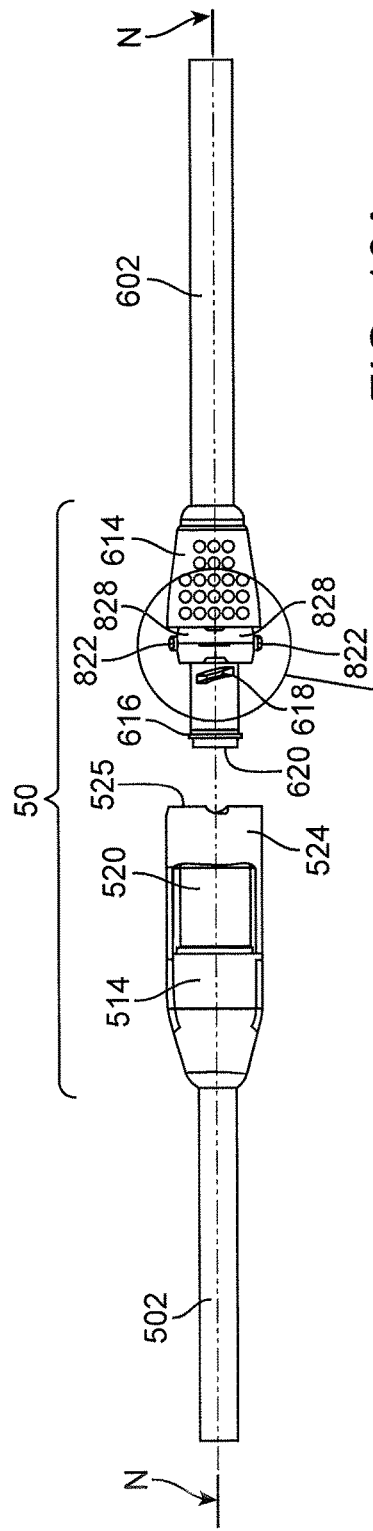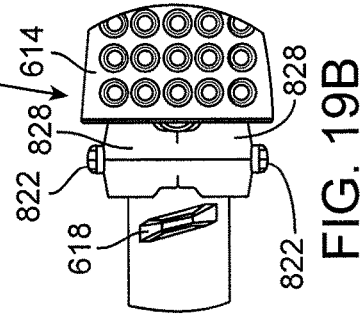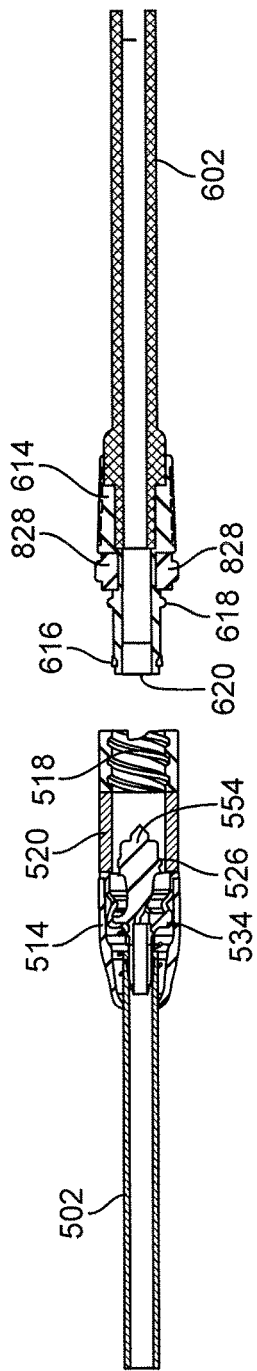

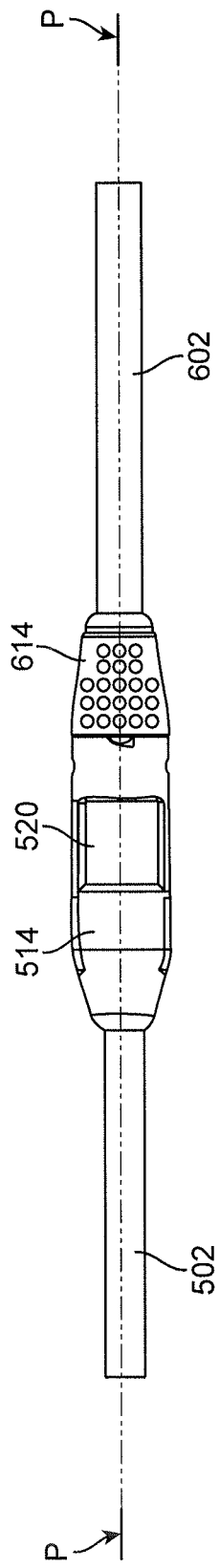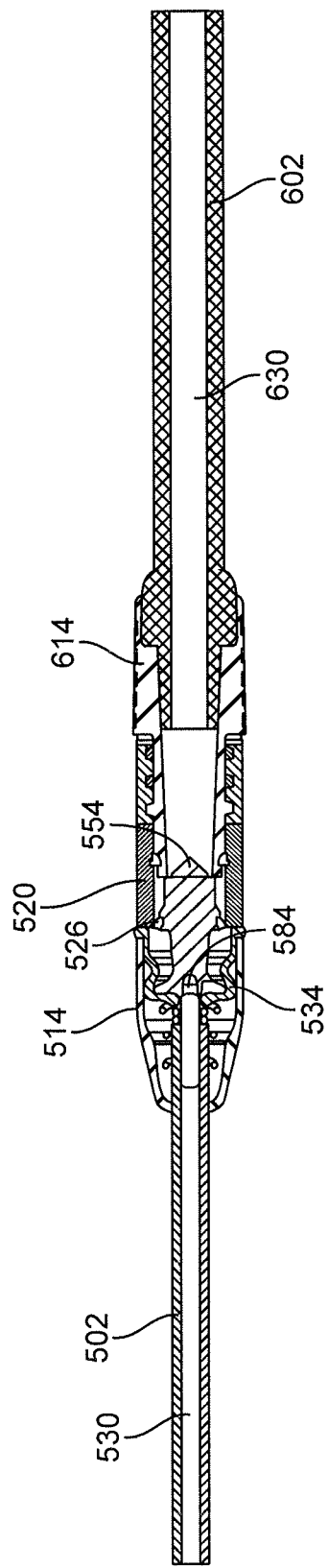

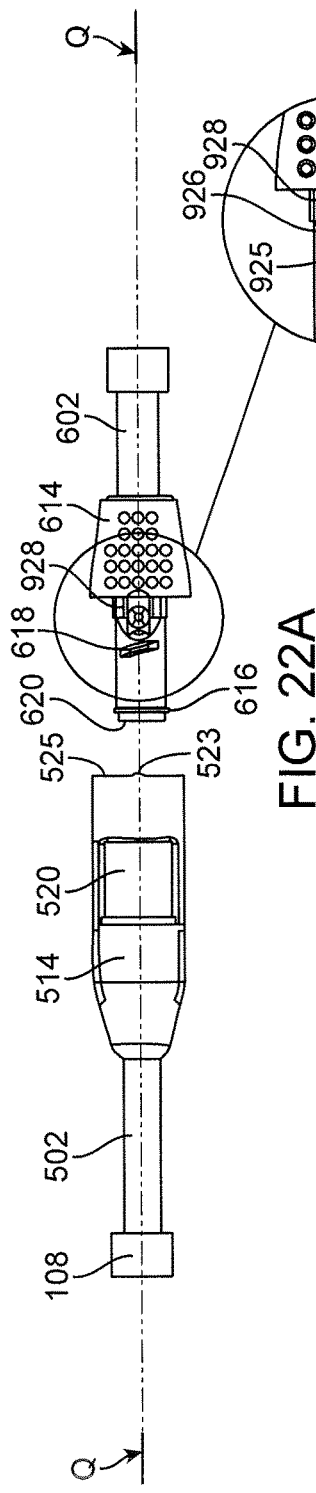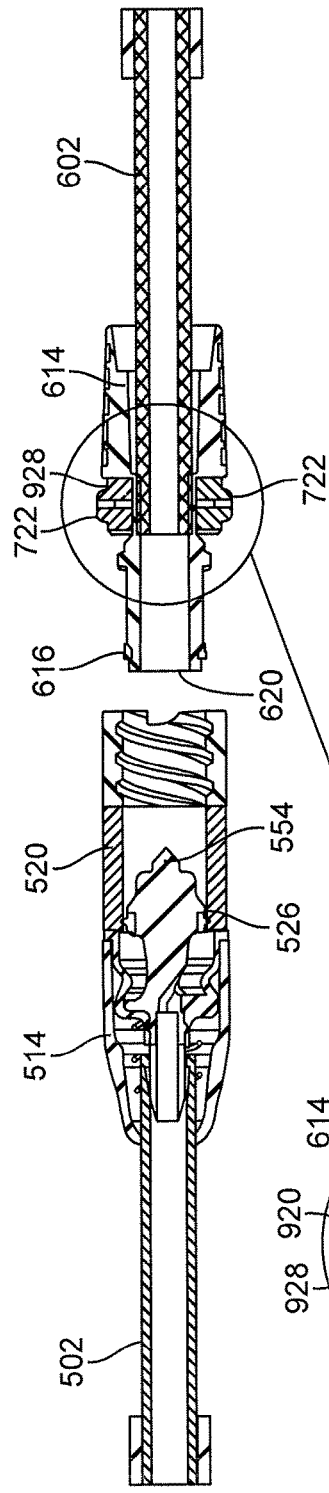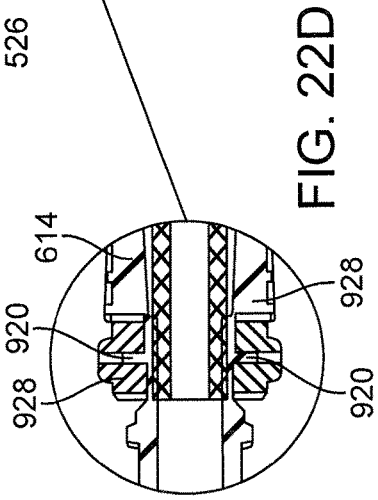
FIG. 22A
FIG. 22B
FIG. 22C
FIG. 22D

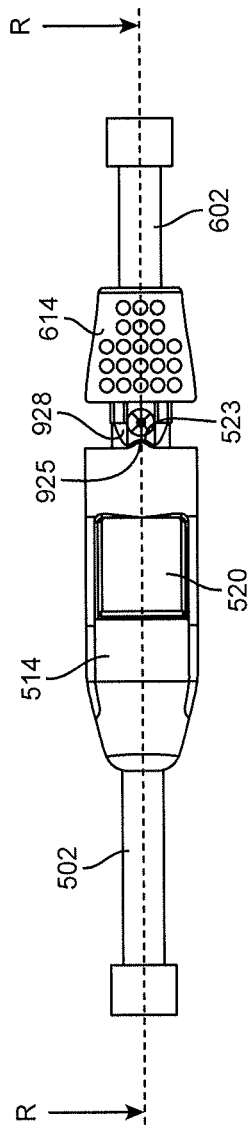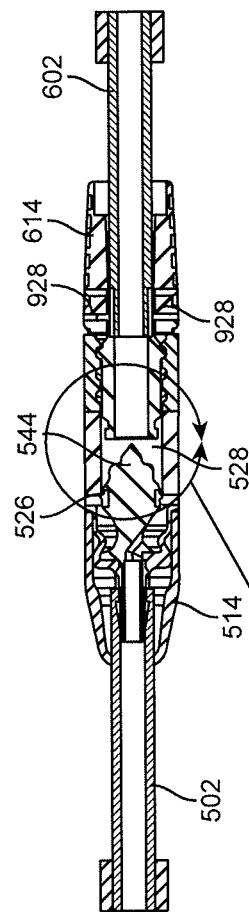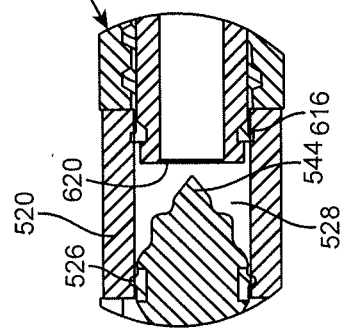
FIG. 23A
FIG. 23B
FIG. 23C

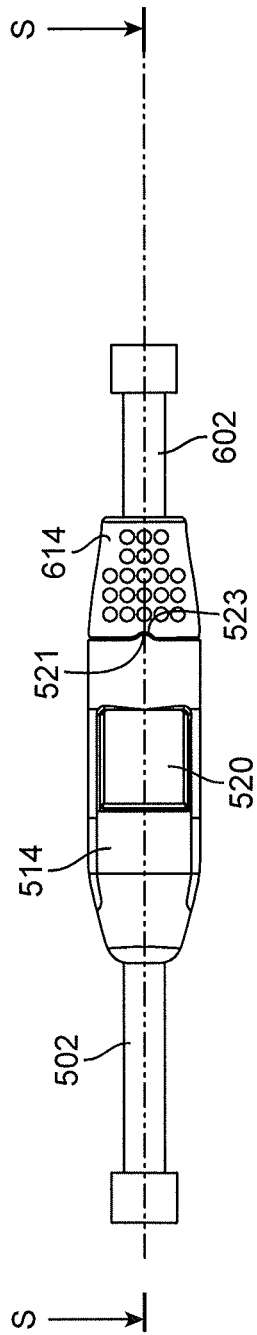
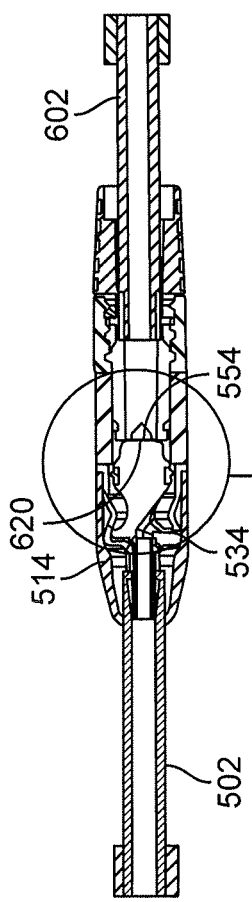
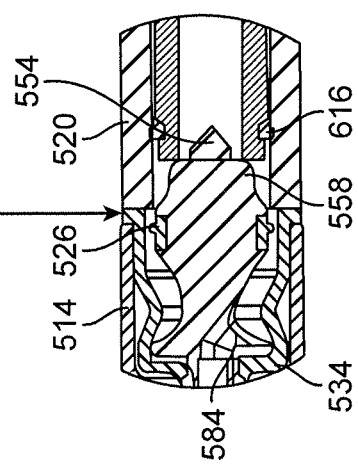
FIG. 24A
FIG. 24B
FIG. 24C

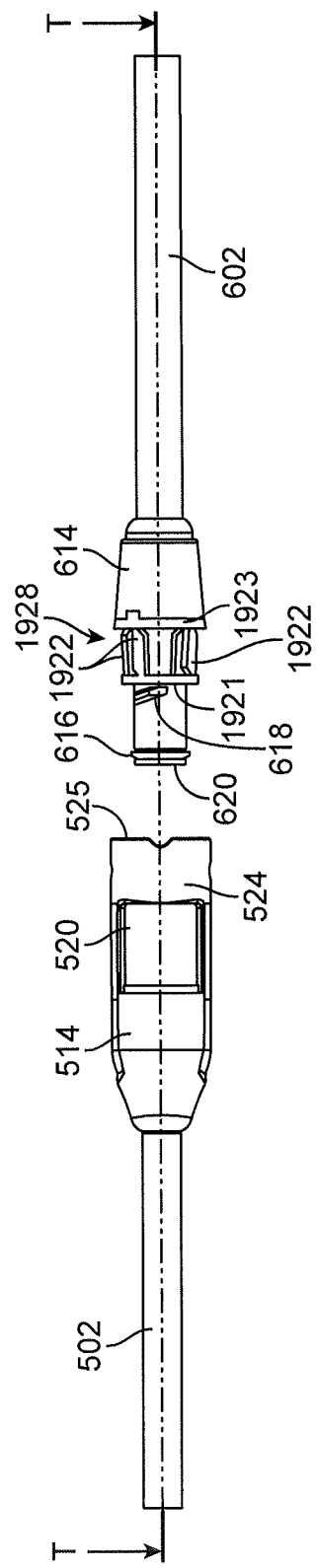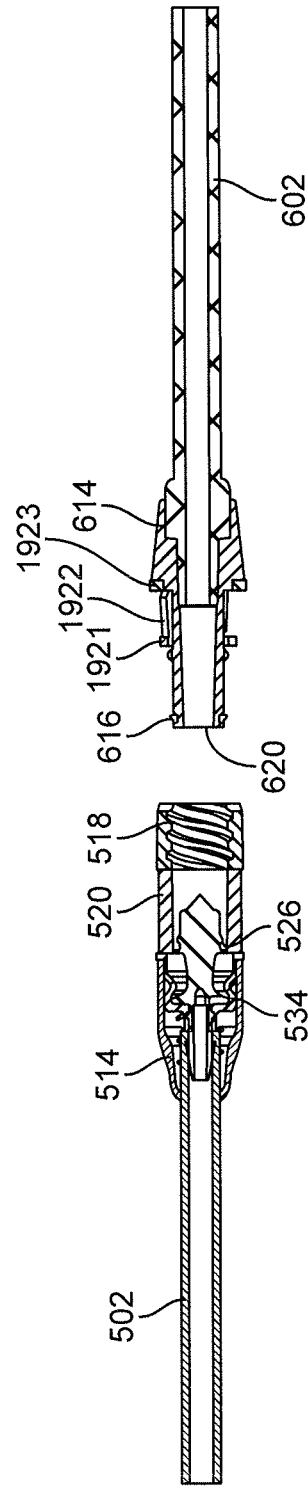
FIG. 25A
FIG. 25B

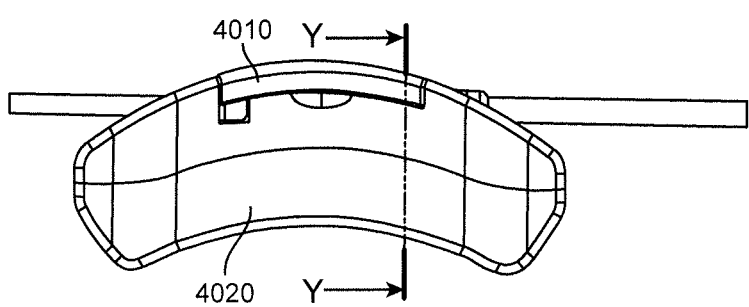
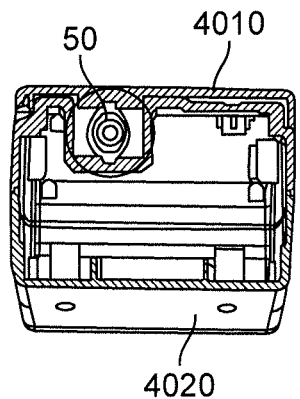
FIG. 31A    FIG. 31B
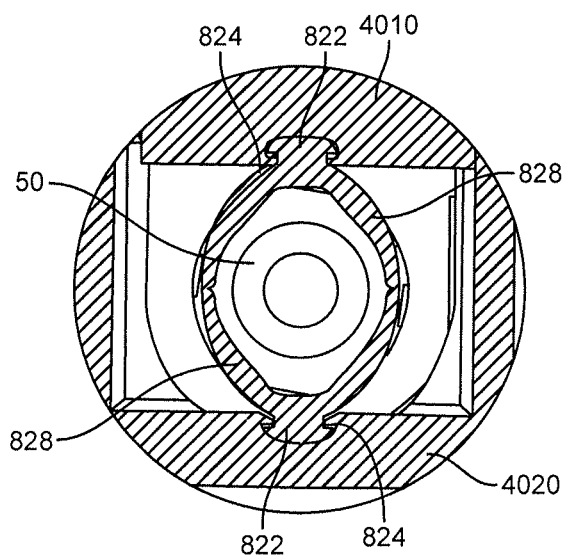
FIG. 31C

CATHETER CONNECTION SYSTEM FOR ULTRAVIOLET LIGHT DISINFECTION

CROSS REFERENCE TO RELATED APPLICATIONS

This application claims the benefit of U.S. Provisional Patent Application No. 62/360,927, filed Jul. 11, 2016, the entire disclosure of which is hereby incorporated by reference herein.

INCORPORATION BY REFERENCE

All publications and patent applications mentioned in this specification are incorporated herein by reference in their entirety to the same extent as if each individual publication or patent application was specifically and individually indicated to be incorporated by reference.

FIELD

This application relates generally to sterilization units, more particularly, sterilization of connectors used in a medical application, for example, during peritoneal dialysis (PD).

BACKGROUND

Catheters are commonly used to infuse fluids into or remove them from various locations in the human body. In many cases these catheters are left in place for weeks or months to provide this access. The longer an indwelling catheter provides this communication between the outside and inside of the body the greater the likelihood microbes such as bacteria, fungi, and viruses can migrate into the body and cause an infection. These infections can be very difficult and costly to treat and can result in a high level of morbidity for patients that have a need for this catheterization. Therefore, there is a high need for preventing the migration of microbes through the catheter and into the body.

The opportunity for microbes to enter the catheter occurs each time the connection point between the indwelling catheter and other equipment used for removing or infusing fluids is opened and closed. One way of preventing the migration of microbes through the catheter into the body is to disinfect the connection point each time it is opened and closed. One particular application for disinfecting this catheter connection point is during peritoneal dialysis.

Peritoneal dialysis (PD) can be used as a treatment for patients with severe chronic kidney disease. Fluid is introduced through a tube in the abdomen and flushed out periodically either while the patient sleeps, in automated peritoneal dialysis, or during regular dialysis sessions through the day, as in continuous ambulatory peritoneal dialysis.

As shown in FIG. 1, a patient undergoing peritoneal dialysis can have an indwelling catheter 4 surgically inserted into the abdomen. A transfer catheter 2 can be attached to the indwelling catheter. The transfer catheter can be replaced, in a sterile environment, such as at a clinic, every few months to a year. Between dialysis sessions, the patient wears the transfer catheter against the body. During dialysis sessions, the transfer catheter can be connected to a drain bag to drain the fluid present in the abdomen and a fresh dialysate bag to introduce fluid to the abdomen. The drain bag and dialysate bags can be attached in series or can be attached in parallel using a Y-shaped solution set catheter 6. Prior to each treatment, the patient connects the tip of the transfer catheter to a new dialysis solution set catheter using rigorous aseptic techniques to maintain sterility. The aseptic technique include the patient and anyone around them wearing a mask, closing doors and windows, turning off fans, and thoroughly washing hands for 2 minutes. Then the patient typically scrubs the opening of the transfer catheter with alcohol, iodine, or a similar antiseptic agent prior to connecting the catheters. The same sterile technique must be employed when disconnecting the catheters as well. If sterility is compromised at any time, the component being used must be replaced and the whole process started again. Once the patient feels confident enough to perform the procedure at home unattended, and after many months of practice, the time to disinfect, connect and start PD takes approximately 20-30 minutes.

This is a complicated and time-consuming process that is highly reliant on patient compliance. If a patient fails to adhere to any of the strict steps of the sterilization procedure, he or she faces a greatly increased risk of a serious infection that targets the peritoneal cavity, commonly referred to as peritonitis. This type of internal infection, if not caught early, may leads to sepsis and death of the patient. Typically, PD patients experience a 50% chance of infection during the first 12 to 18 months and experience 15% mortality/yr directly related to the infection. In addition to seriously endangering the patient's health, infections in peritoneal dialysis are also very costly to treat. The average total charges form a peritonitis hospital stay are roughly $50,000 dollars and the entire annual cost to the healthcare system is around $1.5 billion. Given that the noncompliance rate for a standard PD procedure is around 30%, there is a huge need to help reduce the health and financial burdens of infection.

Ultraviolet (UV) disinfection systems are known in the art. U.S. Pat. Nos. 4,882,496; 7,834,328; 4,620,845; 6,461,568 and U.S. Publication Nos. 2005/0013729 and 2007/0274879, the disclosures of which are incorporated by reference herein in their entireties, describe such systems. However, such systems can be cumbersome, making them difficult for a patient to use. Additionally, such systems tend to rely on UV disinfection for complete disinfection, which can, in the absence of proper components and connectors, limit the effectiveness of the disinfection.

SUMMARY

In some embodiments, an ultraviolet (UV) catheter connection disinfection system is provided. The system comprises a first connector comprising a UV transparent region at a first end of the first connector and a first seal proximal to the UV transparent region; a second connector comprising a leading membrane surface and a second seal for sealing against the UV transparent region at a first end of the second connector, wherein the first end of the second connector is configured to mate with the first end of the first connector in a first disinfection position in which the first seal and the leading membrane surface are blocks between the first and second connectors and a second flow position in which the first seal is deflected and the leading membrane surface is ruptured to allow flow between the connectors; a piercing member configured to pierce the leading membrane surface; and a clip connected to at least one of the first connector and second connector, the clip configured to prevent movement from the disinfection position to the flow position, wherein the clip is configured to be removed or broken by interaction of the clip with a UV disinfection unit.

In some embodiments, the clip is configured to be broken by interaction with the UV disinfection unit. The clip can be configured to be pushed off by interaction with the UV disinfection unit. In some embodiments, the clip is configured to be pulled off by interaction with the UV disinfection unit. The clip can be configured to be collapsed by interaction with the UV disinfection unit. The interaction can comprise closing of a door of the UV disinfection unit. In the disinfection position, a small volume disinfection zone can be bounded by the leading membrane surface, and inner surface of the UV transparent region, the first seal, and the second seal. In some embodiments, the leading membrane surface comprises at least one of metallic foil, a plastic foil, a microporous surface, a semi-porous surface, and a semi-permeable surface. The UV transparent region can comprise at least one of quartz glass, cyclic olefin copolymer, and polymethylpentene, also known by the trade name TPX™. In some embodiments, a second end of the second connector is configured to connect to a tubular member through a sealed connector, the tubular member removable from the second connector while maintaining the seal at the second end of the second connector. The sealed connector can comprise a needleless connector. The sealed connector can comprise a luer connector. The luer connector can be removed along with the tubular member. In some embodiments, the first connector is configured to connect to an indwelling catheter. The second connector can be configured to connect to a solution set catheter. The first and/or second connector can comprise the piercing member. The system can comprise a spring maintaining the first seal in a sealing position within the UV transparent region. The first seal can comprise the piercing member. The clip can be integrally formed with the second connector. In some embodiments, the clip is formed separately from the second connector.

In some embodiments, a method of disinfecting a catheter connection is provided. The method comprises connecting a first end of a first connector with a second end of a second connector such that the connectors are in a disinfection position, the first connector comprising a lumen comprising a UV transparent region; a first sealing member positioned in the UV transparent region and blocking flow through the first connector; the second connector comprising a second sealing member configured to sealingly engage a surface of the UV transparent region; and a leading membrane surface separating a lumen of the second connector from the lumen of the first connector; positioning the connectors in a disinfection unit, wherein positioning the connectors in the disinfection unit causes removal of a clip preventing the connectors from moving into a flow position; exposing the UV transparent region to UV light; and advancing the second connector with respect to the first connector, thereby piercing the leading membrane surface and moving the connectors into a flow position.

In some embodiments, advancing the transfer catheter connector with respect to the solution set connector comprises turning the connector relative to one another. In some embodiments, advancing the transfer catheter connector with respect to the solution set connector also results in piercing the leading membrane surface.

In some embodiments, an ultraviolet (UV) catheter connection disinfection system is provided. The system comprises a first connector comprising a UV transparent region at a first end of the first connector and a sealing plunger positioned proximal to the first end of first connector; a second connector comprising a leading membrane surface and a sealing surface for sealing against the UV transparent region at a first end of the second connector; a piercing member configured to pierce the leading membrane surface; and a deflector configured to deflect the sealing plunger into a flow position, wherein the first end of the second connector is configured to mate with the first end of the first connector in a first disinfection position in which the leading membrane surface is intact and the sealing plunger is blocking flow through the first connector and a second flow position in which the leading membrane surface is punctured by the piercing member and the sealing plunger is deflected into the flow position by the deflection member.

In some embodiments, in the disinfection position a small volume disinfection zone is bounded by the leading membrane surface, and inner surface of the UV transparent region, the sealing surface, and the sealing plunger. The sealing surface can comprise at least one of an o-ring, a wiper shaped blade, and a spring energized seal. In some embodiments, the sealing surface comprises at least one of silicone, butyl rubber, PTFE, and neoprene. The leading membrane surface can comprise at least one of metallic foil, a plastic foil, a microporous surface, a semi-porous surface, and a semi-permeable surface. In some embodiments, the UV transparent region comprises at least one of quartz glass, cyclic olefin copolymer, and TPX™. The system can comprise a stop configured to prevent the system from inadvertently moving from the disinfection to the flow position. The stop can comprise a clip. The system can comprise a spring maintaining the plunger seal in a sealing position within the UV transparent region. In some embodiments, a second end of the second connector is configured to connect to a tubular member through a sealed connector, the tubular member removable from the second connector while maintaining the seal at the second end of the second connector. The sealed connector can comprise a needleless connector. The sealed connector can comprise a luer connector. In some embodiments, the luer connector is removed along with the tubular member. The first connector can be configured to connect to an indwelling catheter. The second connector can be configured to connect to a solution set catheter. In some embodiments, the second connector comprises the piercing member. The piercing member can serve as the deflector. The first connector can comprise the piercing member. The sealing plunger can comprise the piercing member. In some embodiments, the first connector and the second connector comprise threads to hold the connectors together. The sealing surface can comprise the joining of the UV transparent region and the first end of the second connector. In some embodiments, the first connector comprises a sealing actuator configured to advance the sealing plunger against an opening of the UV transparent region. In some embodiments, the sealing plunger and the leading membrane surface are resealable. In some embodiments, the sealing plunger and the leading membrane surface are single use components. In some embodiments, the sealing plunger is resealable and the leading membrane surface is a single use component. In some embodiments, the sealing plunger is a single use component and the leading membrane surface is resealable.

In some embodiments, a method of ultraviolet (UV) disinfection is provided. The method comprises connecting a first end of a first connector with a second end of a second connector such that the connectors are in a disinfection position, the first connector comprising a lumen formed using a UV transparent region; a first sealing member positioned in the UV transparent region and blocking flow through the first connector; the second connector comprising a second sealing member configured to sealingly engage a surface of the UV transparent region; a leading membrane surface separating a lumen of the second connector from the lumen of the first connector; and a piercing member; exposing the UV transparent region to UV light; advancing the second connector with respect to the first connector; piercing the leading membrane surface with the piercing member; and deflecting the first sealing member to allow flow between the first connector lumen and the second connector lumen.

In some embodiments, a method of ultraviolet (UV) disinfection is provided. The method comprises connecting a distal end of a transfer catheter connector with a proximal end of a solution set catheter connector such that the connectors are in a disinfection position, the transfer catheter connector comprising a lumen having a UV transparent region at its distal end; a first sealing member positioned in the UV transparent region and blocking flow through the transfer catheter connector; the solution set catheter connector comprising a second sealing member configured to sealingly engage a surface of the UV transparent region; a leading membrane surface separating a lumen of the solution set catheter connector from the lumen of the transfer catheter connector; and a piercing member; exposing the UV transparent region to UV light; advancing the transfer catheter connector with respect to the solution set connector so that the connectors are in a flow position; piercing the leading membrane surface with the piercing member; and deflecting the first sealing member to allow flow between the transfer catheter connector lumen and the solution set catheter connector lumen.

In some embodiments, advancing the transfer catheter connector with respect to the solution set connector comprises turning the connector relative to one another. In some embodiments, advancing the transfer catheter connector with respect to the solution set connector also results in piercing the leading membrane surface with the piercing member. In some embodiments, advancing the transfer catheter connector with respect to the solution set connector also results in deflecting the first sealing member. In some embodiments, advancing the transfer catheter connector with respect to the solution set connector also results in both piercing the leading membrane surface with the piercing member and deflecting the first sealing member to allow flow between the transfer catheter connector lumen and the solution set catheter connector lumen. The method can further comprise disengaging a stop prior to advancing the transfer catheter connector relative to the solution set catheter connector. Disengaging a stop can comprise removing a c clip. The method can further comprise flowing fresh dialysate from a solution set catheter connected to the solution set catheter connector to the transfer catheter connector. The method can further comprise removing the solution set catheter from the solution set catheter connector while maintaining a seal at a distal end of the solution set catheter connector.

In some embodiments, an ultraviolet (UV) disinfection system for use during peritoneal dialysis is provided. The system comprises a transfer catheter connector comprising a UV transparent region at a distal end of the connector; a valve positioned at a proximal end of the UV transparent region; and a piercing member positioned within the valve; a solution set connector comprising a lumen configured to be fluidly connected to the solution set tubing, a proximal end of the lumen sealed with a barrier, the lumen comprising a seal around a portion of the lumen, wherein a portion of the UV-transparent region is configured to be inserted within a portion of the solution set connector into a first disinfection position in which the barrier is intact and a second flow position in which the barrier is punctured by the piercing member.

In some embodiments, the valve allows passage of the piercing member therethrough and is configured to return to a sealed state upon retraction of the piercing member. The transfer catheter connector can comprise threads configured to mate with threads on the solution set connector. In some embodiments, the UV-transparent region comprises quartz. The piercing member can be configured to extend through the valve upon deflection of the valve towards the piercing member. The transfer catheter connector can comprise a stop configured to interact with a mating feature on the solution set connector.

In some embodiments, an ultraviolet (UV) disinfection system is provided. The system comprises a transfer catheter connector comprising a lumen formed using an UV transparent region at a distal end of the connector; a valve positioned at a proximal end of the UV transparent region and within the lumen; and a piercing member positioned within the connector and separated from the lumen by the valve; a solution set connector comprising a lumen configured to be fluidly connected to the solution set tubing, an insertion tube sized for positioning within the UV transparent region, a barrier over a proximal opening of the insertion tube, a seal around an exterior portion of the insertion tube sized for sealing engagement with an interior surface of the UV transparent region, wherein a portion of the UV-transparent region is configured to be inserted within a portion of the solution set connector into a first disinfection position in which the barrier is intact and a second flow position in which the barrier is punctured by the piercing member.

In some embodiments, a method of ultraviolet (UV) disinfection is provided. The method comprises inserting a distal end of a transfer catheter connector into a proximal end of a solution set connector such that the connectors are in a disinfection position, the transfer catheter connector comprising a lumen formed using an UV transparent region at a distal end of the connector; a valve positioned at a proximal end of the UV transparent region and within the lumen; and a piercing member positioned within the connector and separated from the lumen by the valve, and the solution set connector comprising a lumen configured to be fluidly connected to the solution set tubing, an insertion tube sized for positioning within the UV transparent region, a barrier over a proximal opening of the insertion tube, a seal around an exterior portion of the insertion tube sized for sealing engagement with an interior surface of the UV transparent region; placing the transfer catheter connector and the solution set connector into a UV disinfection unit; activating the disinfection unit; further inserting the transfer catheter connector into the proximal end of the solution set connector such that the connectors are in a flow position; piercing the barrier with the piercing member; and opening a transfer catheter clamp to allow flush of spent dialysate.

In some embodiments, further inserting the transfer catheter connector into the proximal end of the solution set connector such that the connectors are in a flow position comprises turning the connectors relative to one another about 1 full turn. In some embodiments, inserting a distal end of a transfer catheter connector into a proximal end of a solution set connector such that the connectors are in a disinfection position comprises turning the connectors relative to one another about ¼ turn. In some embodiments, inserting a distal end of a transfer catheter connector into a proximal end of a solution set connector such that the connectors are in a disinfection position comprises inserting the distal end of the transfer catheter connector until a stop on the transfer catheter connector engages with a mating feature on the solution set connector. In some embodiments, further inserting the transfer catheter connector into the proximal end of the solution set connector such that the connectors are in a flow position first comprises disengaging the stop from the mating feature.

In some embodiments, an ultraviolet (UV) disinfection unit for a catheter line connection is provided. The unit comprises a housing; a lid shaped to mate with a top open part of the housing, the lid connected to the housing by a hinge; a UV source positioned within the unit; a channel positioned beneath the lid and configured to receive a catheter connection comprising two connectors; a disinfection zone positioned along the channel, the disinfection zone at least partially exposed to the UV source; and a clip release feature configured to interact with a stop feature on the catheter connection to allow flow between the two connectors.

The lid can comprise projections configured to mate with slots in the channel. The projections can comprise the clip release feature and are configured to force the stop feature off of the catheter connection.

In some embodiments, a method for disinfecting a catheter line connection is provided. The method comprises positioning a catheter line connection within a tubing trough of the unit; and closing the lid of the unit, thereby automatically locking the lid and initiating a disinfection cycle, wherein the lid automatically unlocks upon completion of the disinfection cycle.

In some embodiments, a method of using a UV disinfection unit for disinfection catheter connections is provided. The method comprises overdriving the UV lamps at the beginning of a disinfection cycle.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 5a is an illustration of an end view of an embodiment of the solution set catheter of a catheter connection system.

FIG. 5b is an illustration of a cross section view of an embodiment of the solution set transfer catheter from FIG. 5a through line B-B.

FIG. 6b is an illustration of a detailed view of an embodiment of the catheter connection system from FIG. 6a.

FIG. 7b is an illustration of a detailed view of an embodiment of the catheter connection system from FIG. 7a.

FIG. 9b is an illustration of an end view of an embodiment of the catheter connection system from FIG. 9a.

FIG. 9c is an illustration of a cross section view of an embodiment of the catheter connection system from FIG. 9b through line D-D with the connection sealed to prevent fluid flow before disinfection.

FIG. 10a is an illustration of a detailed view of still another alternate embodiment of the catheter connection system.

FIG. 10b is an illustration of an end view of an embodiment of the catheter connection system from FIG. 10a.

FIG. 10c is an illustration of a cross section view of an embodiment of the catheter connection system from FIG. 10b through line E-E.

FIG. 11a is an illustration of a detailed view of yet another alternate embodiment of the catheter connection system.

FIG. 11b is an illustration of an end view of an embodiment of the catheter connection system from FIG. 11a.

FIG. 11c is an illustration of a cross section view of an embodiment of the catheter connection system from FIG. 11b through line F-F.

FIG. 12b is an illustration of an end view of an embodiment of the catheter connection system from FIG. 12a.

FIG. 14a is an illustration of a top view of an embodiment of a catheter connection system.

FIG. 14b is an illustration of a side view of an embodiment of a catheter connection system from FIG. 14a.

FIG. 14c is an illustration of a cross section view of an embodiment of a catheter connection system from FIG. 14b through line I-I.

FIG. 15a is an illustration of a side view of an embodiment of a catheter connection system.

FIG. 15b is an illustration of a cross section view of an embodiment of a catheter connection system from FIG. 15a through line J-J.

FIG. 15c is an illustration of a detail view of an embodiment of a catheter connection system from FIG. 15b.

FIG. 16a is an illustration of a side view of another alternate embodiment of a catheter connection system.

FIG. 16b is an illustration of a cross section view of an embodiment of a catheter connection system from FIG. 15a through line K-K.

FIG. 18a is an illustration of a side view of an embodiment of a catheter connection system.

FIG. 18b is an illustration of a cross section view of an embodiment of a catheter connection system from FIG. 17a through line M-M.

FIG. 18c is an illustration of a detail view of an embodiment of a catheter connection system from FIG. 18b.

FIG. 19a is an illustration of a side view of an embodiment of a catheter connection system.

FIG. 19b is an illustration of a detail view of an embodiment of a catheter connection system from FIG. 19a.

FIG. 19c is an illustration of a cross section view of an embodiment of a catheter connection system from FIG. 19a through line N-N.

FIG. 20b is an illustration of a detail view of an embodiment of a catheter connection system from FIG. 20a.

FIG. 21a is an illustration of a side view of another alternate embodiment of a catheter connection system.

FIG. 21b is an illustration of a cross section view of an embodiment of a catheter connection system from FIG. 21a through line P-P.

FIG. 22a is an illustration of a side view of another alternative embodiment of a catheter connection system.

FIG. 22b is an illustration of a detail view of an embodiment of a catheter connection system from FIG. 22a.

FIG. 22c is an illustration of a cross section view of an embodiment of a catheter connection system from FIG. 22a through line Q-Q FIG. 22d is an illustration of a detail view of an embodiment of a catheter connection system from FIG. 22c.

FIG. 23a is an illustration of a side view of an embodiment of a catheter connection system.

FIG. 23b is an illustration of a cross section view of an embodiment of a catheter connection system from FIG. 23a through line R-R.

FIG. 23c is an illustration of a detail view of an embodiment of a catheter connection system from FIG. 23b.

FIG. 24a is an illustration of a side view of an embodiment of a catheter connection system.

FIG. 24b is an illustration of a cross section view of an embodiment of a catheter connection system from FIG. 24a through line S-S.

FIG. 24c is an illustration of a detail view of an embodiment of a catheter connection system from FIG. 24b.

FIG. 25a is an illustration of a side view of another alternative embodiment of a catheter connection system.

FIG. 25b is an illustration of a cross section view of an embodiment of a catheter connection system from FIG. 25a through line T-T.

FIG. 28b is an illustration of a detail view of a UV disinfecting device from FIG. 28a.

FIG. 28c is an illustration of an end view of a catheter connection system and a UV disinfecting device from FIG. 28a.

FIG. 31a is an illustration of a side view of a catheter connection system of FIG. 20a-20c and a UV disinfecting device.

FIG. 31b is an illustration of a cross section view of a UV disinfecting device from FIG. 31a through line Y-Y.

FIG. 31c is an illustration of a detail view of a catheter connection system and a UV disinfecting device from FIG. 31b.

DETAILED DESCRIPTION

Figure 1:
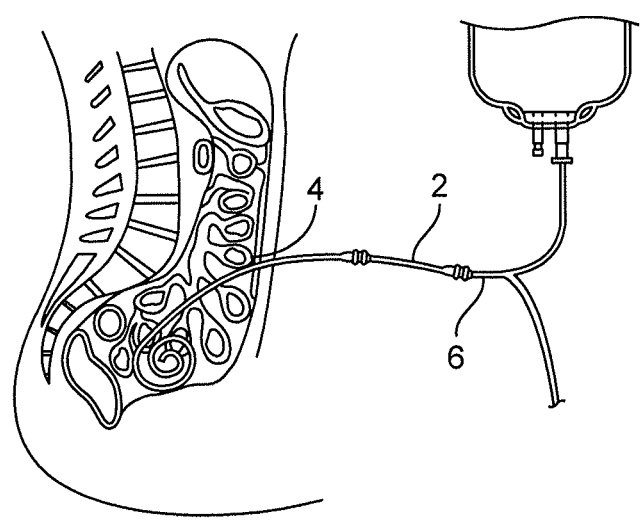
FIG. 1 is an illustration of a conventional peritoneal dialysis setup.

Embodiments of systems and methods for disinfecting catheter connections using ultraviolet (UV) light are disclosed herein. The catheter connectors can be connected in a connection position, without allowing flow between the catheters, disinfected, and then be moved into a flow position, in which flow is allowed between the two catheters. Disinfection comprises irradiating the connection between the connected catheters through a UV-transparent windows at an end of one of the connectors. The portion of the catheter connection to be irradiated, the disinfection zone, advantageously includes the portion of each connector that is exposed to contamination. This is made possible by seals and/or valves positioned at or near the ends of both connectors. These seals and/or valves allow the connectors to be connected in an non-disinfected or dirty state and sufficiently disinfected as the seal and/or valves prevent contamination from entering portions of the catheter connections that are not irradiated. The catheter connection also has seals and/or valves that allow the connection to move from the disinfection position to a flow position while maintaining the sterility of the catheters. Further details of such catheter connections are provided below and in U.S. patent application Ser. No. 15/074,854, filed Mar. 18, 2016 ("the '854 application"), the entirety of which is incorporated by reference herein.

To ensure user compliance with disinfecting the catheter connection prior to flowing liquid through it, the catheter connectors can include a mechanism or interference (e.g., a clip, tab, stop, etc.) to stop the catheter connection at the disinfection position and require that mechanism to be overridden before movement to the flow position. In some embodiments, the mechanism comprises tactile feedback (e.g., in the form of mating features as shown in FIG. 15 of the '854 application) that requires additional or different force to be exerted to move the catheter connection into the flow position. In other embodiments, placing the catheter connection in a disinfection unit removes the interference preventing the catheter connection from moving into the flow position. Thus, only after placement in the disinfection unit can the catheter connectors be moved into the flow position.

The catheter connectors can be connected in the disinfection position and then placed in the unit. Placement in the unit and/or closing of the lid can automatically cause the unit to start a disinfection cycle. In such embodiments, the disinfection system contains no user operated power or activation button. Instead, in these embodiments, a detection system, method or process is used to allow or inhibit system operation.

On one aspect, a step accomplished by the user to load a disinfection chamber is detected by the system to automatically initiate a disinfection cycle or process. One specific example of a disinfecting unit of this configuration is the sliding lid chamber design illustrated and described with respect to FIGS. 27A and 27B of U.S. Provisional Application 62/360,922, filed Jul. 11, 2016, and entitled "Point of Care Ultraviolet Disinfection System". Once a manifold, component, adapter or connector is properly positioned within the unit (FIG. 27A), disinfection begins when the user completes the step of sliding the lid to the closed position (FIG. 27B).

In some embodiments, detection by the system includes one or more steps or a proper sequence of steps to be completed before initiating the disinfection cycle. In some other embodiments, detection used to initiate a disinfection cycle includes indications from both the user and the system. One example includes a user step of aligning a catheter connection over a chamber and then inserting first one end into an alignment slot before snapping a second end into another portion of the chamber. One or both of these user actions may be used by a sensor to indicate that the action was completed or completed correctly according to sequence. For example, a proximity sensor or position detection sensor could be placed in the alignment slot in the preceding example. When the user correctly inserts the catheter connection, the sensor provides a signal to the disinfection unit controller to indicate the correct presence of the catheter connection. Other examples are possible such as a latching mechanism, mechanical, magnetic, optical or other type that is used to indicate that the chamber lid is closed or otherwise indicate proper interaction of a catheter connection with an appropriate portion of a disinfecting unit. In still other embodiments with moving lids or portions of a chamber must engage before operation of the unit, the system may include one or more of sensors, limit switches, position indicators, intended to trigger or otherwise permit a disinfection operation to proceed. In a similar way, a lid or chamber component may include one or more mechanical, electrical, optical, or magnetic feature or component used to ensure, guide or indicate, including electronically to a system controller, the presence of a permitted or properly inserted catheter connection. Optionally or additionally, one or more of these features may be adapted to prevent removal of component undergoing disinfection until the entire disinfection sequence is completed.

In one specific aspect, a disinfection unit embodiment is adapted and configured to detect whether a permitted or authorized catheter connection is present in the unit. If a permitted or authorized catheter connection is detected, then a disinfection cycle starts automatically without further user action. As a result of the detection capability of the disinfection unit, the auto cycle mode would only work when the unit detects a permitted or authorized catheter connection. Since this disinfection unit is configured without an ON/OFF button, the unit's detection capability prevents use/misuse by a user attempting to operate the unit improperly or with non-permitted or unauthorized catheter connection. The interoperability of the unit with a permitted or authorized catheter connection may be accomplished in a number ways. The detection system may utilize colored band/s, patterns, stripes, bar codes, metallic rings, or radiopaque materials alone or in combination with other electrically, optically or magnetically recognizable or detectable features. These detectable features are included in permitted or authorized catheter connections so as to be detectable by electrical, optical or magnetic or other appropriate sensors within the UV light source housing, disinfecting unit or other component of an embodiment described herein.

In some embodiments, the detection capability includes an input interface such as an optical reader (i.e., a barcode scanner or other device which is capable of reading a computer-readable symbols) appropriately integrated into the disinfection unit so as to read/detect a computer readable authorization, authentication or permission symbol placed in a detectable location on a permitted or authorized catheter connection. In still other embodiments, an input interface may also include an inductive or near field communication system, a magnetic card reader, or an optical camera which is capable of retrieving information stored within a magnetic stripe or a computer-readable code, respectively, on a permitted or authorized catheter connection. In one specific example, the detection capability or system of a disinfection unit includes a QR code indicating a permitted or authorized catheter connection capable of being detected and deciphered using an optical camera and computer-executable software operable by the disinfecting unit to retrieve information from the QR code. In one specific example, the detection capability or detection system of a disinfection unit incorporates the use of an RFID tag and appropriate RFID reader. In this implementation of the detection system, operation of the disinfection unit proceeds only when the detection capability indicates a permitted or authorized RFID tag on a catheter connection present in the disinfection unit.

In some embodiments, closing the door of the disinfection unit automatically locks the door. This automatic locking feature can prevent the user from removing the catheter connection prior to completion of a UV disinfection cycle. In some embodiments, the catheter connection cannot be removed from the disinfection unit until the disinfection cycle has completed. For example, in some embodiments, the door locks and unlocks automatically at the end of the disinfection cycle.

In some embodiments, running the disinfection cycle comprises an initial period of overdriving the UV lamps. An existing problem with the use of UV lamps for disinfection is the time it takes for the lamps to warm up. This warm up period can last up to several minutes, during which the lamps have not reached their peak disinfection ability. This increased time for disinfection inconveniences the user and risks user non-compliance. Overdriving the lamps solves these problems. In some embodiments, overdriving the lamps comprises providing 100%, 50%, 25% of the specify input current to the lamp in order to overdrive it for a period of 30 seconds, 22 seconds, 10 seconds, five seconds. Then the current is dropped to the specified level and maintained at that level. In some embodiments, this can be done alternately by over driving the voltage in a similar manner for a similar period time and then dropping the voltage to the specified level. Either of these techniques for result in a greater amount of UV light being produced by the UV lamp in the initial overdriven time period, and the lamp being warmed up to it steady-state in a shorter period of time.

Further details about the disinfection unit can be found below and in U.S. patent application Ser. No. 14/857,522, filed on Sep. 17, 2015, and entitled "Ultraviolet Disinfection Unit" ("'722 Application"). The '722 application describes features such as the unit shape, unit materials, features allowing a disinfection zone of the transfer catheter to be properly positioned within the unit, ambidextrous positioning, light blocks, the tubing trough, lid close sensor, power button safety feature, exposure chamber, and operating parameters.

Figure 2:
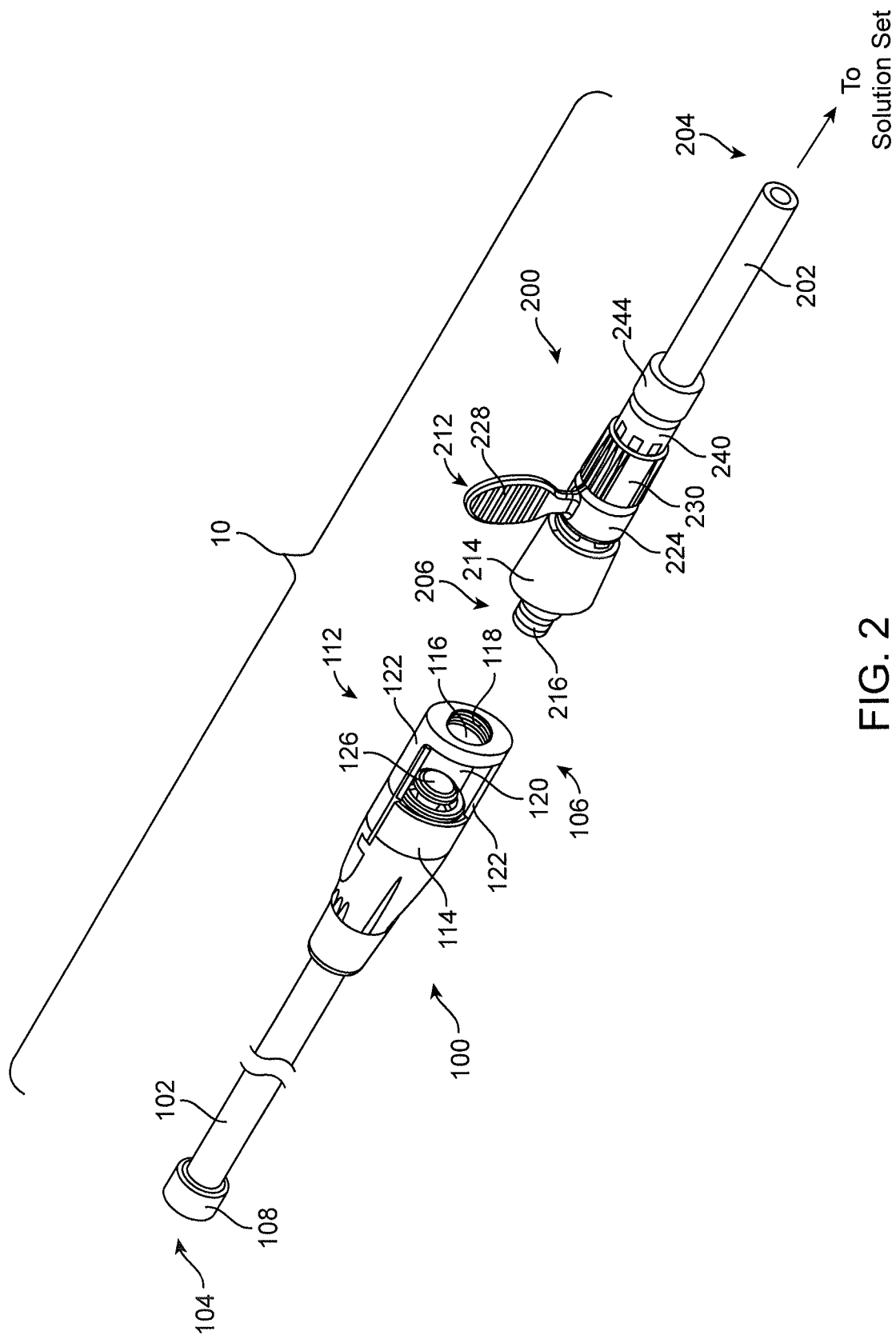
FIG. 2 is an illustration of an embodiment of a catheter connection system.
Figure 3:
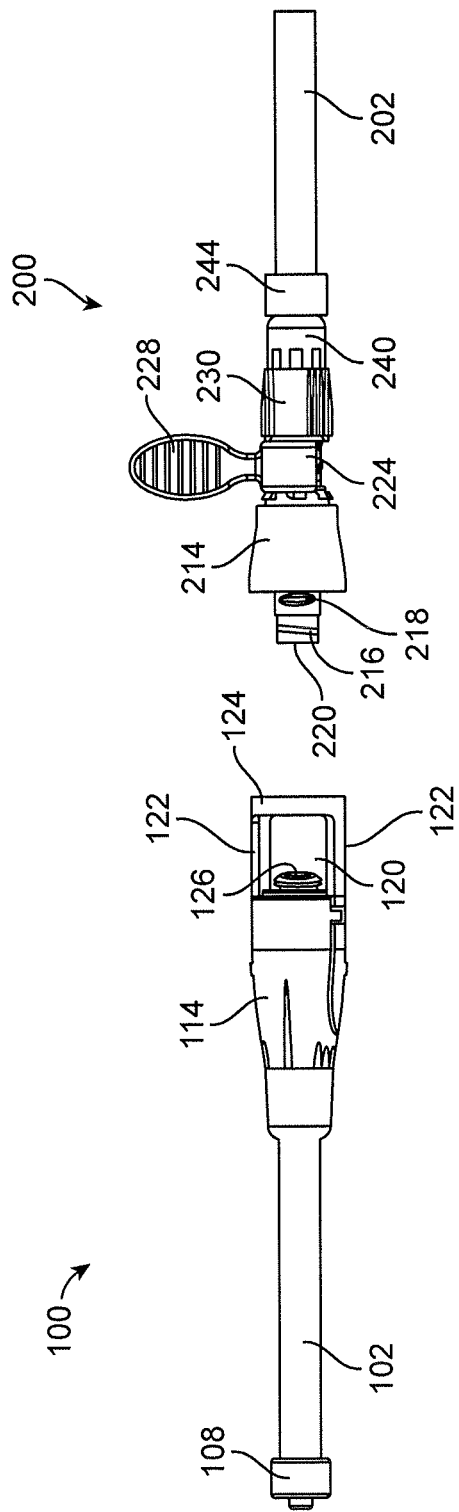
FIG. 3 is an illustration of a side view of an embodiment of a catheter connection system.

Embodiments of the catheter connection system disclosed herein can be used by peritoneal dialysis (PD) patients. FIG. 2 illustrates an embodiment of a catheter connection system 10 that can be used like the transfer catheter 2 and solution set catheter 6 of FIG. 1. The transfer catheter 100 of the catheter connection system 10 of the current invention comprises a tubular body 102, a first end 104 and a second end 106. The transfer catheter 100 comprises a first connector 108 positioned at or near the first end 104, and a second connector 112 positioned at or near the second end 106. Referring also to FIG. 3, the second connector 112 comprises a connector body 114, an end retainer 124, and one or more struts 122 which connect the end retainer 124 to the connector body 114. A UV transparent section 120 is constrained between the connector body 114, the end retainer 124 and the struts 122. The struts 122 are configured to allow UV light to be directed to the UV transparent section 120 from one or more directions without creating any shadows or blocking the UV light from covering the entire transparent section 120. FIG. 2 shows the second connector 112 comprising two struts, but other configurations are also possible. For example, the second connector 112 can comprise 1, 3, 4, 5, or more struts 122. In some embodiments, the struts 122 comprise square edges, as shown in FIG. 2. Other configurations are also possible. For example, the struts 122 may comprise chamfered edges.

Inside the UV transparent section 120 is a sealing plunger 126 which can be actuated to seal off the inside of the UV transparent section 120 from the inside of the connector body 114 and the rest of the fluid path as will be explained in detail below.

The solution set catheter 200 of the catheter connection system 10 comprises a tubular body 202, a first end 204, and a second end 206. The solution set catheter 200 comprises a male connector 212 positioned at or near the second end 206, and is connected to a solution set (not shown) at the first end 204. The male connector 212 is configured to connect to the second connector 112 of the transfer catheter 100. The male connector 212 comprises a connector hub 214, a leading membrane surface 220, a sealing surface 216 and one or more securing threads 218. The leading membrane surface 220 is configured to be easily positioned inside the UV transparent section 120 of the transfer catheter 100, the sealing surface 216 is configured to seal against the inside of the UV transparent section 120 of the transfer catheter 100 and the securing thread 218 is configured to engage with the threads 118 on the inside of the end portion 124 of the transfer catheter 100 to provide a means for securely attaching the solution set catheter 200 to the transfer catheter 100.

The sealing surface 216 can comprise any one of a number of sealing methods well known to those skilled in the art, including, but not limited to, one or more o-rings, wiper shaped blades, spring energized seals, etc. The sealing material of the sealing surface 216 can be any number of sealing materials well known to those skilled in the art including but not limited to silicone, butyl rubber, PTFE, neoprene, etc. The leading membrane surface 220 can comprise any number of sealing materials well known to those skilled in the art including but not limited to metallic or plastic foil and it can be attached to the connector hub 214 via adhesive, dip coating, over-molded, etc. The UV transparent section can comprise any number of UV-transparent substances known to those skilled in the art, such as, but not limited to, quartz glass, cyclic olefin copolymer (e.g., Topas®), and Mitsubishi chemicals TPX™.

The solution set catheter 200 also comprises a c clip 224, a barb hub 230, a needleless connector 240 and a male luer connector 244. The c clip 224 is positioned between the connector hub 214 and the barb hub 230 and prevents relative motion between the barb hub 230 and the connector hub 214 while it is in place. Other mechanisms for preventing relative motion between the barb hub 230 and the connector hub 214 are also possible (e.g., mating protrusions/recesses on the two connectors). The needleless connector 240 and the male luer connector 244 provide a means of selectively attaching and providing fluid flow between the tubular body 202 to the barb hub 230 as will be explained further herein. The needleless connector 240 and male luer 244 can be any one of a number of readily available connectors that are available from numerous suppliers such as Qosina.

Figure 4B:
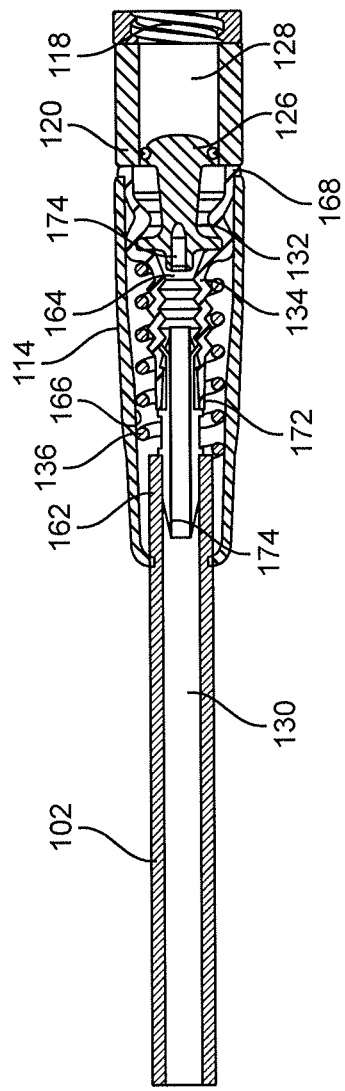
FIG. 4b is an illustration of a cross section view of an embodiment of the transfer catheter from FIG. 4a through line A-A.
Figure 4A:
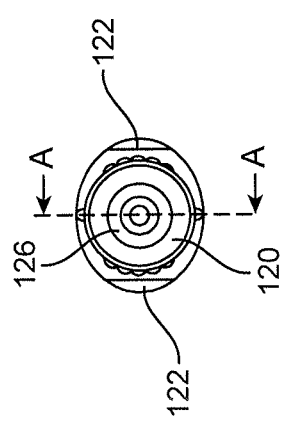
FIG. 4a is an illustration of an end view of an embodiment of the transfer catheter of a catheter connection system.

Referring now to FIG. 4b, the cross section of the connector body 114 is shown to contain the sealing plunger 126, a flexible accordion seal 134, a compression spring 136 and the distal end 162 of the tubular body 102. One end of the compression spring 136 is constrained by the inside 166 of the connector body 114 and the other end is pushing against the flexible accordion seal 134. The flexible accordion seal 134 in turn presses against a piston 132 that is part of the sealing plunger 126 and opposite the sealing edge of the sealing plunger 126. In this manner, the compression spring 136, absent any other input, maintains the sealing plunger 126 position inside the UV transparent section 120 and isolates the lumen 130 of the tubular body 102 and the inside 164 of the flexible accordion seal 134 from the inside of the UV transparent section 120. This isolation provides a small controlled volume 128 of the inside of the UV transparent section that is potentially exposed to microorganisms when the second connector 112 is not connected to the solution set connector 212. This small controlled volume 128 can serve as the disinfection zone of the connector system. The volume of the disinfection zone 128 can be about 0.25-0.55 cc, for example about 0.4 cc. Resilient members other than compression springs can also be used to maintain the sealing plunger 126 position inside the UV transparent region 120. The distal end 168 of the flexible accordion seal 134 can also be constrained between the connector body 114 and the UV transparent section 120 to provide a fluid tight connection between them. The proximal end 172 of the flexible accordion seal 134 can be connected directly to the tubular body 102 or can be connected to the tubular body 102 using a standard hose barb connector 174. In either manner of connection, an enclosed fluid pathway is provided from the second end 106 of the second connector 112 to the lumen 130 of the tubular body 102. A groove 174 can also be provided in the piston 134 to ensure that fluid can flow past the piston when it is compressed against the flexible accordion seal 134.

Referring now to FIG. 5b, the cross section of the connector hub 214 is shown with internal threads 248 which are configured to receive the external threads 232 of the barb hub 230. The end of the hollow barb hub 236 is also shown with a piercing member 234 positioned inside of the leading membrane surface 220. It can be seen that there is a continuous enclosed fluid pathway from inside face 252 of the leading membrane surface 220 through the inside of the connector hub 214, the barb hub 230, the needleless connector 240 and the male luer 244 to the lumen 230 of the tubular body 202. When the sterile solution set packaging (not shown) is opened the leading membrane surface 220 maintains the sterility of this fluid pathway as there are no openings for microorganisms.

Figure 6A:
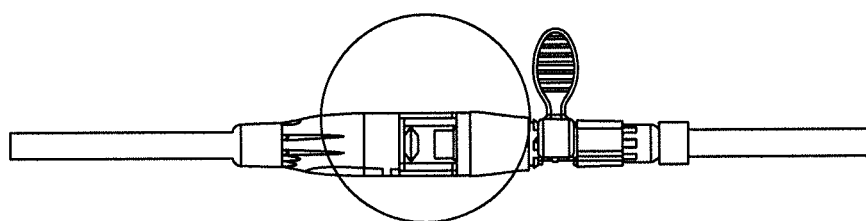
FIG. 6a is an illustration of a side view of an embodiment of a catheter connection system.
Figure 6B:
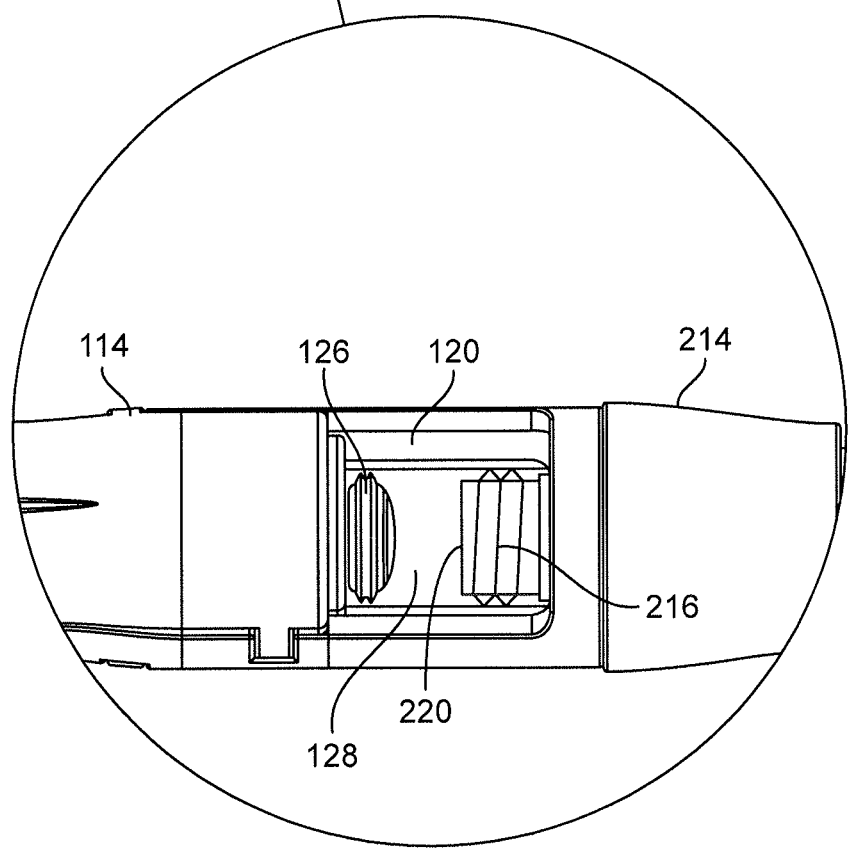
Figure 7A:
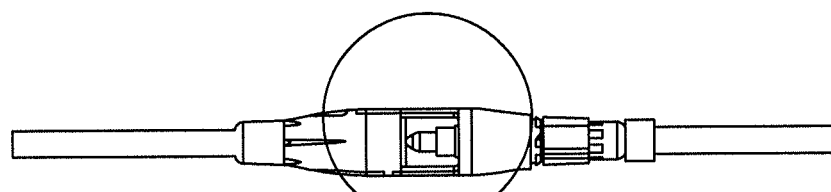
FIG. 7a is an illustration of a side view of an embodiment of a catheter connection system.
Figure 7B:
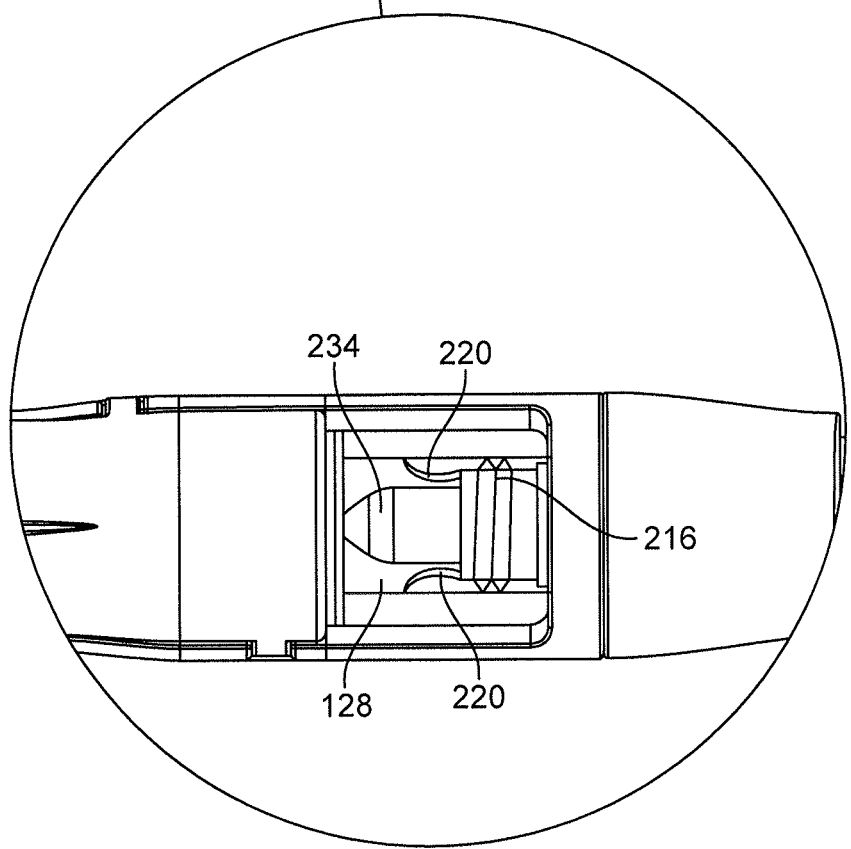
Figures 7C, 7D:
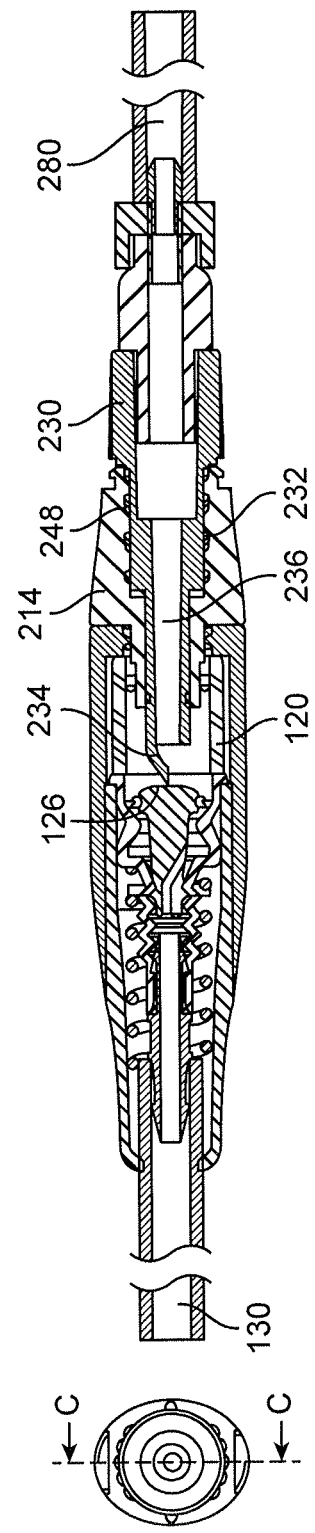
FIG. 7c is an illustration of an end view of an embodiment of the catheter connection system.
FIG. 7d is an illustration of a cross section view of an embodiment of the catheter connection system from FIG. 7c through line C-C.

FIGS. 6a and 6b show the transfer catheter 100 connected to the solution set catheter 200. The sealing surface 216 of the solution set catheter 200 is inserted inside the UV transparent section 120 of the transfer catheter 100 and seals against the inner surface, the securing threads 218 (see FIG. 3) of the connector hub 214 engage with the threads 118 of the end retainer 124 of the second connector 112 to maintain the connection of the solution set catheter 200 to the transfer catheter 100. In this configuration, the UV transparent section 120, the sealing surface 216 and the sealing plunger 126 create a small contained volume 128 that is isolated from the outside and from both the transfer catheter 100 inner lumen 130 and the solution set catheter 200 inner lumen 280. This small contained volume 128 comprises all of the inner space that may have been exposed to microorganisms prior to the connection; and it provides a UV-transparent pathway for UVC light to penetrate and kill any microorganisms that may have contaminated the space or the end of the solution set catheter 200 before the connection was made (including the leading membrane surface 220 and any other portion of the connector hub 214 that is in between the leading membrane surface 220 and the sealing surface 216). With this configuration, it is very easy for the user to place the catheter connection system 100 into a UVC generating apparatus (not shown) for delivery of UVC to the disinfection zone 128 to kill any contamination from microorganisms. Alternately the user can direct UVC light into the disinfection zone 128 using an appropriate UVC light apparatus without first placing the catheter connection system 100 into the UVC apparatus. Exemplary UV light apparatuses are described in U.S. application Ser. No. 14/857,522, filed Sep. 17, 2015, entitled "Ultraviolet Disinfection Unit" and International Application No. PCT/US15/25352, filed Apr. 10, 2015, and entitled "Connector Disinfection System".

Referring to FIGS. 7a-7d, the catheter connection system 10 is shown without the c clip 224 and with the barb hub 230 advanced towards the transfer catheter 100. The c clip 224 can be easily removed from the catheter connection system 10 by the user by grasping and pulling the tab 228.

In this embodiment, the barb hub is advance by rotating wherein the external threads 232 of the barb hub 230 engage the internal threads 248 of the connector hub 214. It will be obvious to those skilled in the art that the use of threads and a rotating motion are just one of many possible means for advancing the barb hub 230 relative to the connector hub 214. Any means can be used in the current invention for advancing the barb hub 234 relative to the connector hub 214 including but not limited to a straight axial movement, without departing from the current invention. For example, in some embodiments, axial motion can be used to move the barb hub 234 relative to the connector hub 214. When advanced, the piercing member 234 (e.g., barb) of the barb hub 230 penetrates the leading membrane surface 220 and creates an opening in the leading membrane surface through which fluid can flow. In the same manner of advancing the barb hub 230 relative to the connector hub 214 and penetrating the leading member surface 220 with the piercing member 234, the advancing piercing member 234 then applies a force on the sealing plunger 126 to overcome the force from the compression spring 136 and advance the sealing plunger 126 out of the UV transparent section 120. In this manner, the small contained volume 128 that was previously isolated (by the UV transparent section 120, sealing plunger 126, and sealing surface 216) and disinfected from all microorganisms by UVC light is now open for fluid flow from the inner lumen 130 of the transfer catheter 100 to the inner lumen 280 of the solution set catheter 200. The flow of fluid from one catheter to the other is not constrained to one direction only and can flow in either direction in the configuration shown in FIGS. 7a-7d.

With the catheter connection system 10 described above, a patient can make a connection to a transfer catheter 100 with a new solution set catheter 200 as is done in the typical PD procedure without the need to go through all the numerous contamination prevention steps as are typically required with the current standard of care. Rather than following those time consuming steps with the catheter connection system 10 of the current invention, the patient can quickly and easily make the connection as described herein, then disinfect the small contained volume 128 using UVC light, and then open the small contained volume 128 by penetrating the seal on the solution set catheter 200 and opening the sealing plunger 126 on the transfer catheter 100 in order to complete the fluid exchange needed for the PD procedure. The catheter connection system 10 both greatly reduces the number of steps needed for PD and greatly increases the efficacy of the disinfection at the connection, the combination of which reduces the complexity and increases the safety of PD.

Figure 8:
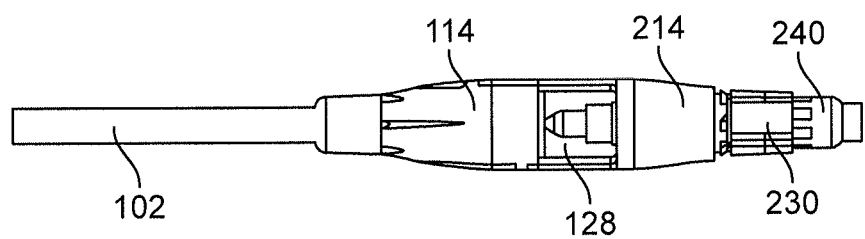
FIG. 8 is an illustration of a side view of an embodiment of a catheter connection system.

After the fluid exchange, it is typical for the solution set catheter 200 to be disconnected from the transfer catheter 100; then the solution set catheter 200 and used solution set are discarded and the second end 106 of the transfer catheter 100 is capped to reduce the chance of microorganisms entering the inner lumen 130. Between the steps of disconnecting the solution set catheter 200 and capping the transfer catheter 100 there is another opportunity for microorganisms to enter the inner lumen 130. Referring to FIG. 8, with the catheter connection system 10 of the current invention, the solution set catheter 200 is not completely disconnected from the transfer catheter 100 after fluid exchange. Rather, the male luer connector 244 and attached tubular body 202 are disconnected from the needleless connector 240 and they are then discarded along with the used solution set. As is well known by those skilled in the art the needleless connector 240 has a seal septum (not shown) which seals the needleless connector 240 and therefore the inner lumen 130 of the catheter connection system 10 as the male luer 244 is removed preventing any contamination on the inner lumen 130 by microorganisms. The remainder of the solution set catheter 200 is left attached to the transfer catheter 100 until the next PD procedure is needed. At that time, the solution set catheter 200 is disconnected from the transfer set catheter 100 by counter rotating the connector hub 214. As the connector hub 214 moves relative to the transfer catheter 100 the piercing member 234 moves relative to the sealing plunger 126 and the sealing plunger 126 reenters the UV transparent section 120 sealing off the inner lumen 130. It will be obvious to those skilled in the art, that the relative positions of the sealing surface 216, the sealing plunger 126 and the piercing member 234 can be configured to ensure that the sealing plunger 126 reenters the UV transparent section 120 and seals it from the inner lumen 130 before the sealing surface 216 exits the other end of the transparent section 120 to ensure that no microorganisms can enter through the UV transparent section 120 and into the inner lumen 130. In this manner, the inner lumen 130 of the transfer catheter 100 is only exposed to potential air and or touch contamination by microorganisms at the beginning of each PD procedure when the solution set catheter 200 is disconnected.

The use of the needleless connector 240 and male luer connector 244 for disconnecting the solution set from the solution set catheter 200 is not the only manner to leave the solution set catheter 200 attached to the transfer catheter 100 to prevent opening the connection and creating the possibility for microorganism contamination at the end of the PD procedure. U.S. Pat. No. 8,038,643 discloses one possible alternate method that includes a connector system whereby a plug is advanced into the first end 204 of the solution set catheter 200 sealing the inner lumen 280 prior to disconnecting the solution set catheter 200 from the used solution set. This method can be also used prevent contamination of the inner lumen space of the current invention. Those skilled in the art will know of methods, other than those described herein for, without departing from the current invention, disconnecting a portion of the solution set catheter 200 from the catheter connection system 10 of the current invention without opening the connection between the transfer catheter 100 and the solution set catheter 200, or otherwise allowing potential contamination by microorganisms of the inner lumen 130.

In some embodiments, the sealing plunger of the transfer catheter connector is a reusable (resealable) element. In some embodiments, the sealing plunger is a single use component, and is replaced between uses. The leading membrane surface can also be a reusable or resealable element. In some embodiments, the leading membrane surface is a single use component.

It will be obvious to those skilled in the art that the current invention is not limited to use in just PD procedures, but can be applied to any procedure where there is an indwelling catheter line going into the body where periodic connection and disconnections need to be done to the external end of the indwelling catheters for the purpose of infusing or removing fluid from the body through the indwelling catheter. Such procedures include Foley catheters placed in the bladder, intravascular lines placed either peripherally or centrally into the vascular system, transpareneteral nutrition tubes, esophageal or tracheal tubes and the like. In any of these procedures the potential for contamination of the inner region of the body that the catheter line or equivalent is placed can be reduced by use of the current invention.

Figure 9A:
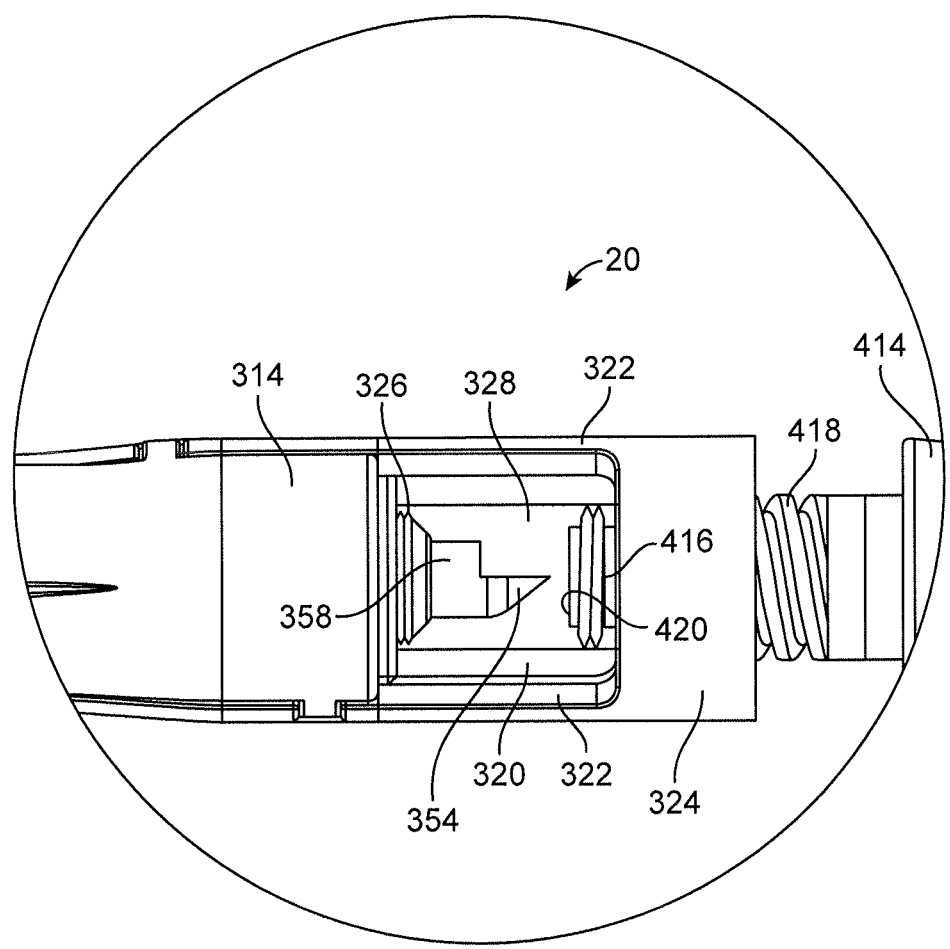
FIG. 9a is an illustration of a detailed view of an alternate embodiment of the catheter connection system.
Figure 9D:
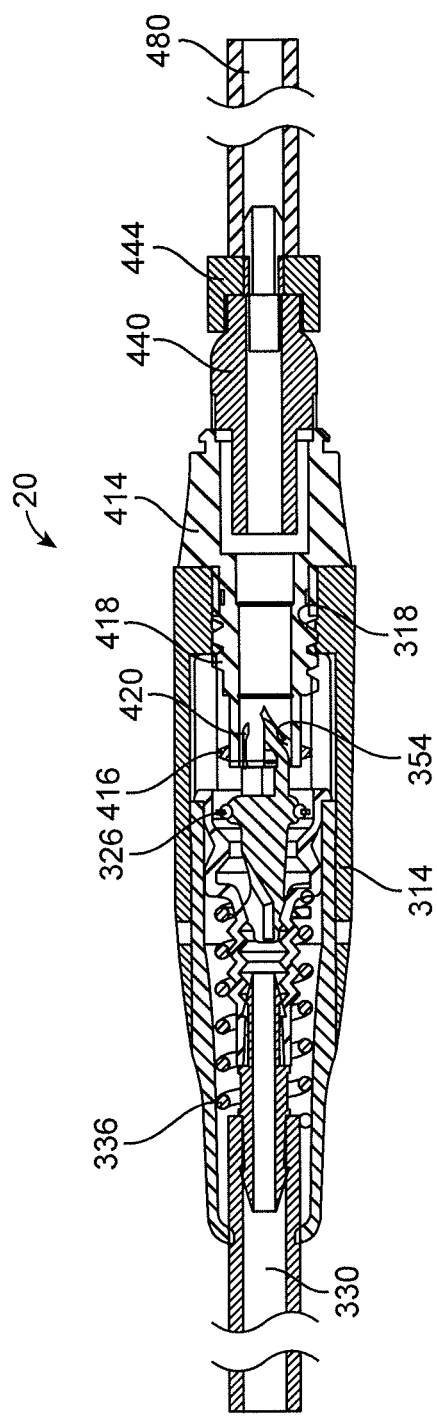
FIG. 9d is an illustration of a cross section view of an embodiment of the catheter connection system from FIG. 9b through line D-D with the connection unsealed to allow fluid flow after disinfection.

The above description describes just one particular embodiment of the current invention. There are many other embodiments possible without departing from the intention of the current invention. One alternate embodiment is show in FIGS. 9a-9c. The catheter connection system 20 of this embodiment includes a sealing plunger 326 that is configured with a piercing member 354. In this embodiment, the connector hub 414 of the solution set catheter engages with the UV transparent section 320 sufficiently for the sealing surface 416 to seal against the inside of the UV transparent section 320 and the leading membrane surface 420 of the connector hub 414 along with the sealing plunger 326 and the UV transparent section 320 create a small contained volume 328. After the small contained disinfection zone volume 328 has been disinfected with UVC light the connector hub 414 is further advanced into the UV transparent section 320 by rotating which advances the external threads 418 on the connector hub 414 along the internal threads 318 of the connector body 314. This advancement forces the leading membrane surface 420 against the piercing member 354 which pierces the leading membrane surface 420 as shown in FIG. 9d. Still further advancement of the connector hub 414 relative to the connector body 414 advances the connector hub 414 against the sealing plunger stop 358 to overcome the force of the compression spring 336 and push the sealing plunger 326 out of the UV transparent section 320. Fluid can then flow back and forth from the inner lumen 330 of the transfer catheter to the inner lumen 480 of the solution set catheter. Removal of the connector hub 414 from the connector body 314 will remove the force on the sealing plunger stop 358 allowing the compression spring 356 to advance the sealing plunger 326 back into the UV transparent section 320 to seal of the UV transparent section from the inner lumen 330. As in the previously described embodiment, the position of the sealing plunger stop, the sealing plunger 326, and the sealing surface 416 are configured such that the sealing plunger 326 will seal against the inside of the UV transparent surface 320 before the sealing surface 416 is withdrawn from the UV transparent section 320 to prevent contamination of the inner lumen 330.

It will be apparent to those skilled in the art that the embodiment shown in FIGS. 9a-9d has fewer components in the solution set catheter than the previously disclosed embodiment described herein. Fewer components generally results in the advantage of a more reliable and less expensive system.

Referring to FIGS. 10a-10c, an alternate embodiment of the catheter connection system 1010 is shown. The connector body 1114 of this embodiment has a seal actuator 1150 which is configured to advance a seal 1126 against an opening 1160 of a UV transparent section 1120. The seal actuator 1150 is comprised of an extended arm 1152 which connects the seal actuator 1150 to the seal 1126 through the flexible accordion membrane 1134. The flexible accordion membrane 1134 seals off around the extended arm 1152 preventing any fluid leak. The seal actuator 1152 is configured for the user to selectively seal and unseal the opening 1160 of the UV transparent section 1120. The catheter connection system 1010 also includes a connector hub 1214, a c clip 1224 and a barb hub 1230. The connector hub 1214 is configured with a leading membrane surface 1220, and the barb hub 1230 is configured with a piercing member 1234 that is position adjacent to the leading membrane surface 1220. When the seal 1126 is advanced against the opening 1160, the seal 1126 the UV transparent section 1120 and the leading membrane surface 1220 create a small controlled volume 1128 that can be disinfected with UVC light. As with previously described embodiments, after disinfection, the c clip 1224 is removed so that the barb hub 1230 can be advanced and the piercing member 1234 can penetrate the leading membrane surface 1220. The seal actuator 1150 is retracted unsealing the opening 1160 in the UV transparent section 1120 allowing fluid to flow to and from the inside of the tubular body 1102 and to and from the inside of the tubular body 1202. In this embodiment, the user is easily able to control the flow of fluid by actuating the seal actuator 1150.

Another alternate embodiment of the current invention is shown in FIGS. 11a-11c. The catheter connector system 2010 comprises a UV transparent section 2120 that has a side opening 2160. The side opening 2160 is covered with a flexible membrane 2134 which is sealed to the UV transparent section 2120 by the connector body 2114 and one or more supporting ribs 2122. In this embodiment, actuation of the seal actuator 2150 forces a ball 2152 against the flexible membrane 2134 such that the flexible membrane 2134 seals against the inside surface of the UV transparent section 2120. The flexible membrane 2134, UV transparent section 2120 and the leading membrane surface 2220 together create a small contained volume 2128 that can be disinfected with UVC light that is directed towards the small contained volume 2128 from one or more directions. After disinfection, the c clip 2224 is removed so that the barb hub 2230 can be advanced and the piercing member 2234 can penetrate the leading membrane surface 2220. The seal actuator 2150 is retracted releasing the force on the ball 2152 and allowing the flexible membrane 2134 to unseal from the inside of the UV transparent section 2120 allowing fluid to flow to and from the inside of the tubular body 2102 and to and from the inside of the tubular body 2202. In this embodiment, the user is easily able to control the flow of fluid by actuating the seal actuator 2150.

Figure 12A:
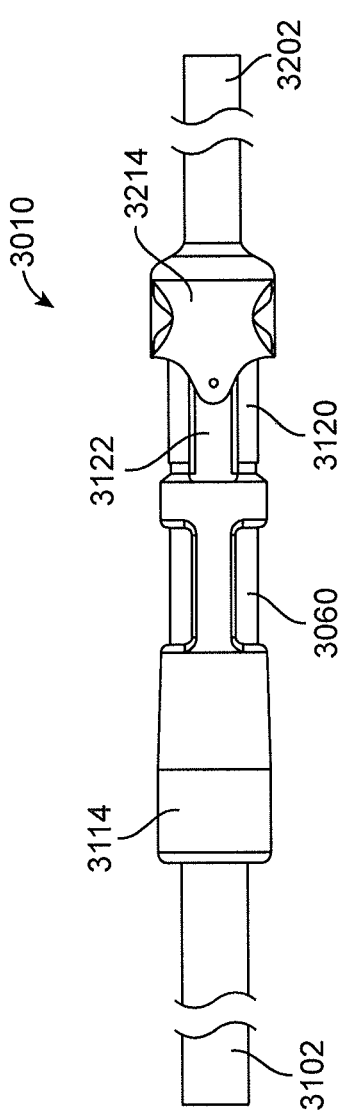
FIG. 12a is an illustration of a detailed view of another alternate embodiment of the catheter connection system.
Figure 12C:
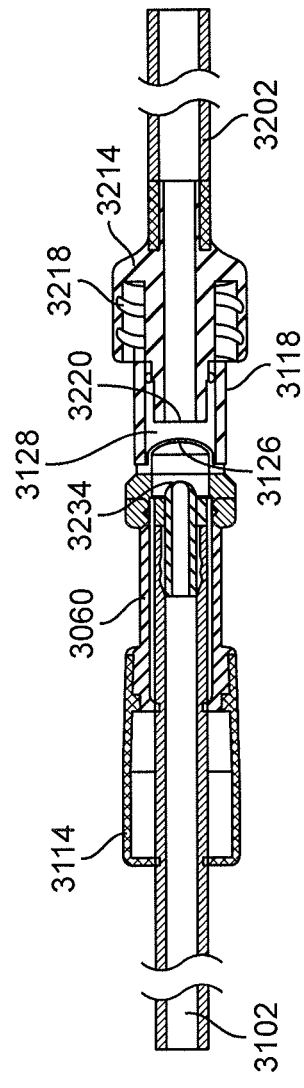
FIG. 12c is an illustration of a cross section view of an embodiment of the catheter connection system from FIG. 12b through line G-G.
Figure 12B:
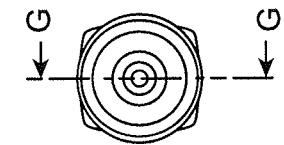

Yet another embodiment of the current invention is shown in FIGS. 12a-12c. The catheter connection system 3010 is comprised of dome seal 3126 that is position between the UV transparent section 3120 and the connector body 3114. The dome seal 3126, the UV transparent section 3120, and the leading membrane surface 3220 create a small contained volume 3128 that can be disinfected with UVC light. After disinfecting the small contained volume 3128 the connector hub 3214 is rotated advancing the leading membrane surface 3220 through a slit in the dome valve 3126 as the internal threads 3218 on the connector hub 3214 engage the external thread 3118 on the connector body 3114. After the leading membrane surface 3220 passes through the dome valve 3126 it is forced over the piercing member 3234 which penetrates the leading membrane surface 3220 allowing fluid to flow to and from the tubular body 3102 and to and from the tubular body 3202. The dome valve 3126 is configured such that the slit will close and reseal the tubular body 3102 from the UV transparent section 3120 when the connector hub 3214 is separated from the connector body 3114. The connector body 3114 is configured with a depressed section 3060 that helps the user securely grasp the connector body 3114 to advance and retract the connector hub 3214.

Figure 13A:
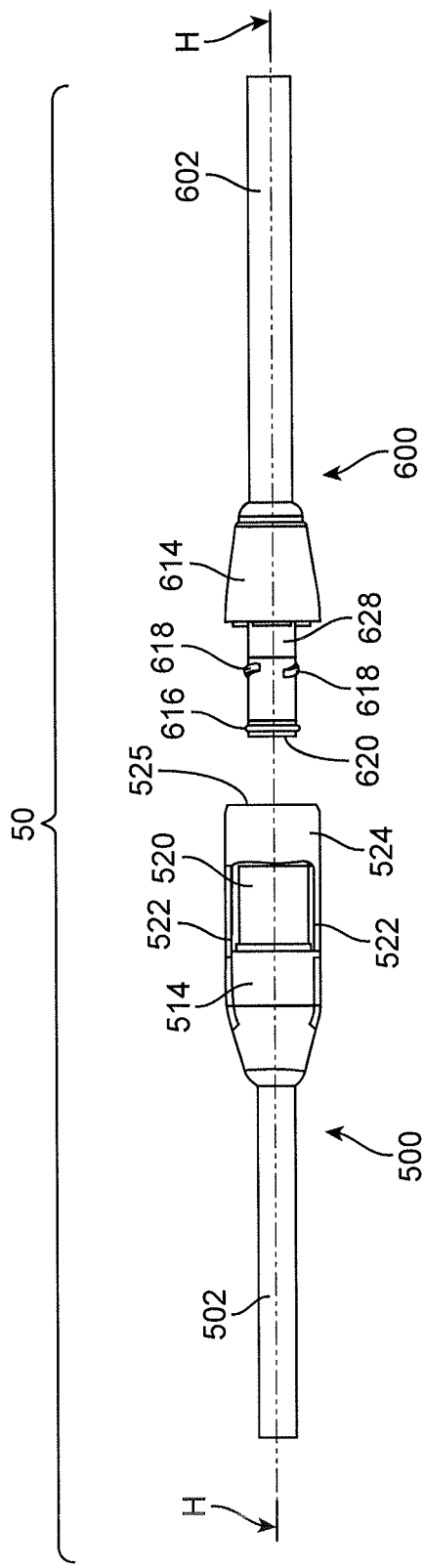
FIG. 13a is an illustration of a side view of another alternate embodiment of a catheter connection system.
Figure 13B:
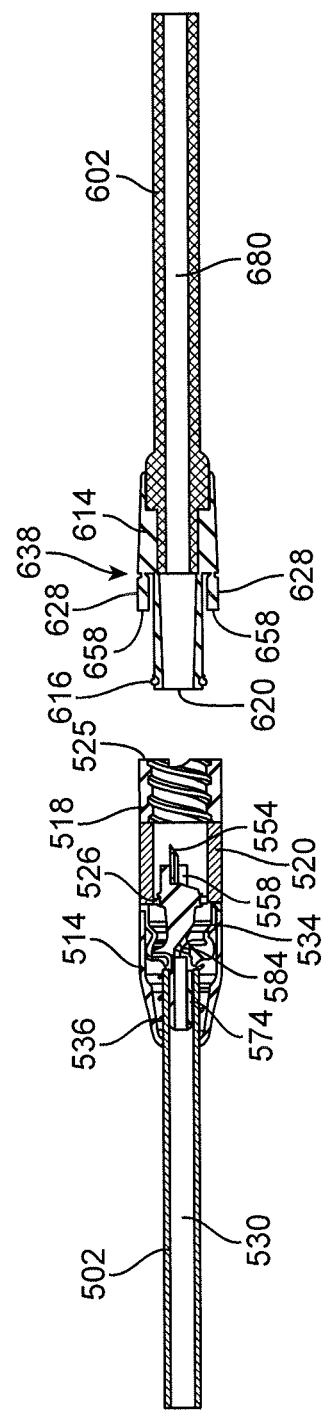
FIG. 13b is an illustration of a cross section view of an embodiment of a catheter connection system from FIG. 13a through line H-H.
Figure 17A:
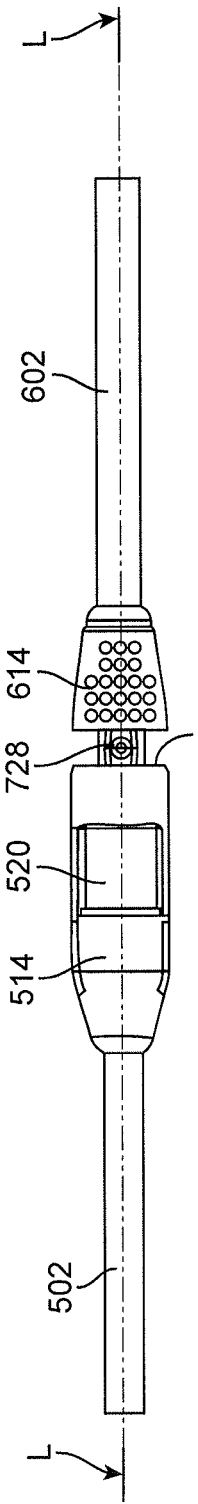
FIG. 17a is an illustration of a side view of an embodiment of a catheter connection system.
Figure 17B:
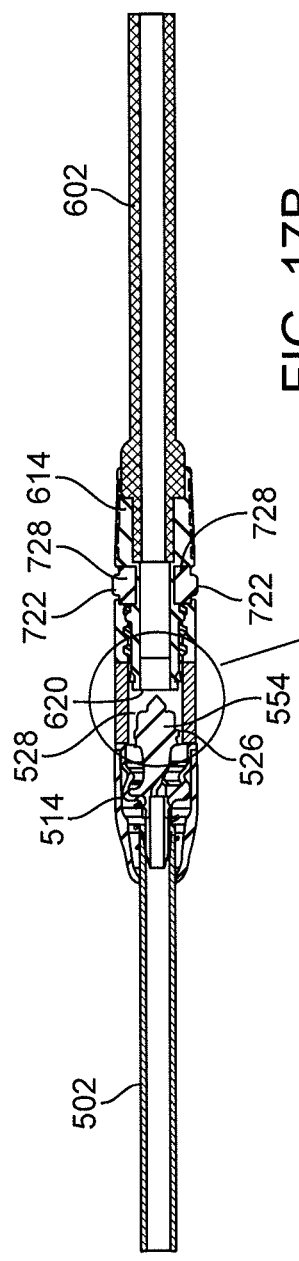
FIG. 17b is an illustration of a cross section view of an embodiment of a catheter connection system from FIG. 17a through line L-L.
Figure 17C:
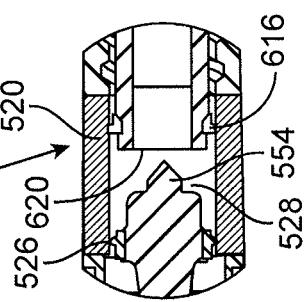
FIG. 17c is an illustration of a detail view of an embodiment of a catheter connection system from FIG. 17b.
Figure 20A:
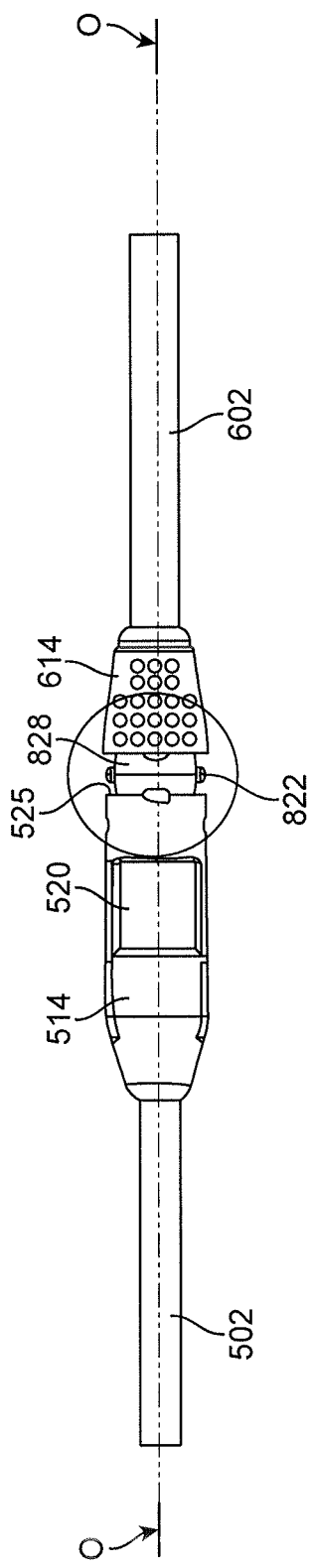
FIG. 20a is an illustration of a side view of an embodiment of a catheter connection system.
Figure 20B:
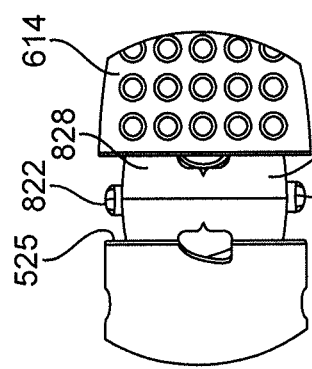
Figure 20C:
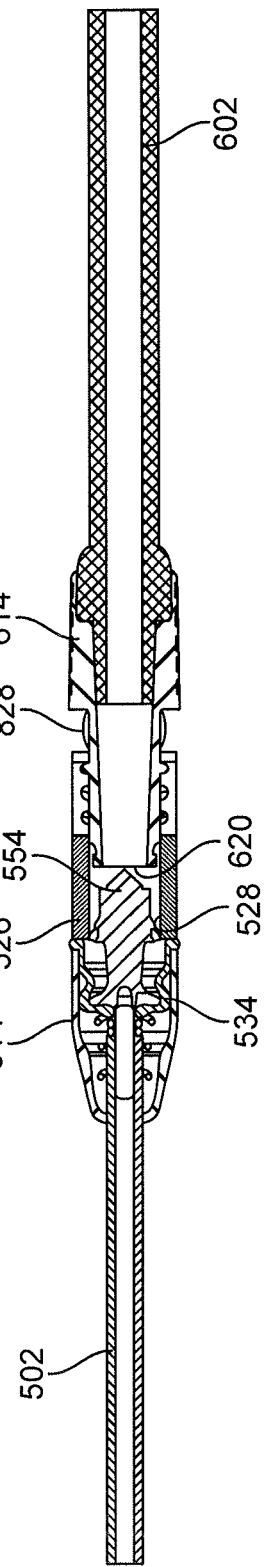
FIG. 20c is an illustration of a cross section view of an embodiment of a catheter connection system from FIG. 20a through line O-O.
Figure 26A:
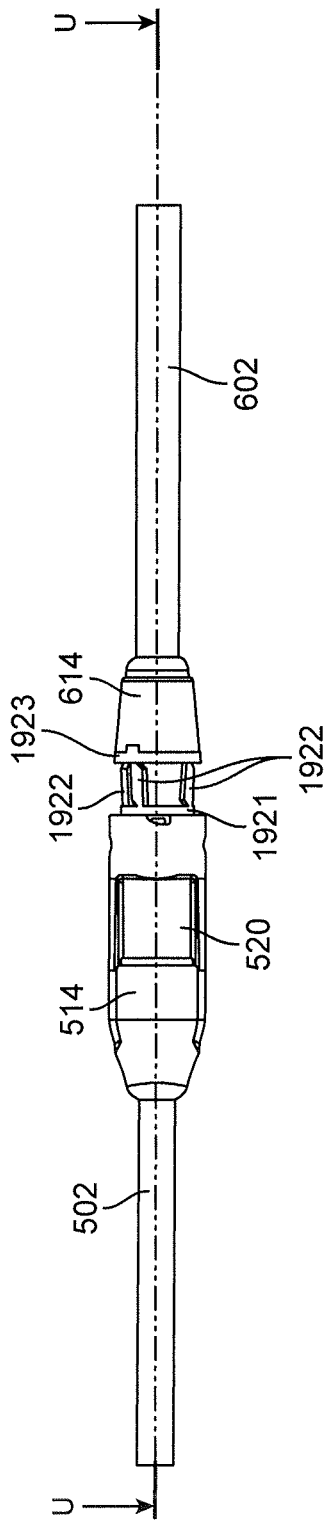
FIG. 26a is an illustration of a side view of an embodiment of a catheter connection system.
Figure 26B:
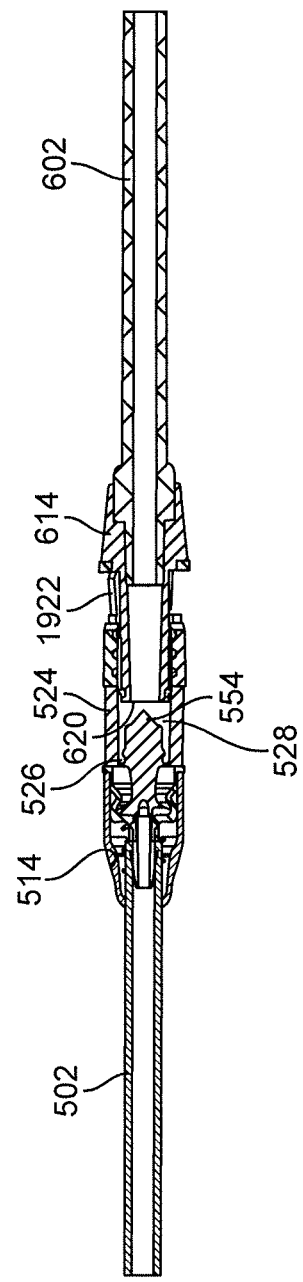
FIG. 26b is an illustration of a cross section view of an embodiment of a catheter connection system from FIG. 26a through line U-U.

FIGS. 13a and 13b illustrate another alternative embodiment of a catheter connection system 50 comprised of a transfer catheter 500 and a solution set catheter 600. The transfer catheter 500 comprises a tubular body 502, a connector body 514, an end retainer 524, and one or more struts 522 which connect the end retainer 524 to the connector body 514. A UV transparent section 520 is constrained between the connector body 514, the end retainer 524 and the struts 522. The solution set catheter 600 comprises a tubular body 602, a connector hub 614, a leading membrane surface 620, a sealing surface 616 and one or more securing threads 618.

Inside the UV transparent section 520 of the transfer catheter 500 is a sealing plunger 526 seals off the inside of the UV transparent section 520 from the inside of the connector body 514 and the rest of the fluid path through the plunger groove 584 and the tubular body lumen 530. As can be seen also now to FIG. 14a-14c, the solution set catheter 600 is shown partially engaged with the transfer catheter 500, by engagement of the securing threads 618 on the solution set catheter 600 with threads 518 on the inside of the end retainer 524. The connector body 614 has one or more stop clips 628 that are integrally molded with the connector body 614 and configured to stop the advancement of the solution set catheter 600 relative to the transfer set catheter 500 when the leading edge 658 of the stop clip 628 engages the face 525 of the end retainer 524. In this position the leading membrane surface 620 and the sealing surface 616 of the solution set catheter 600 along with the sealing plunger 526 create a small controlled volume 558 within the UV transparent section 520. This small controlled volume 528 is isolated from the solution set lumen 680 by the leading membrane surface 620 and from the transfer catheter lumen 530 by the sealing plunger 526 and represents all of the area that could have been contaminated before connection that needs to be disinfected before opening access to the lumens for fluid exchange. The stop clips 628, molded as part of the connector body 614, are not easily removed by the user. The stop clips 628 are specifically design to only be removed by the UV disinfecting unit as will be described later herein. It will be appreciated that the stop clips can be on either connector body 614 or connector body 514.

The leading membrane surface 620 can comprise any number of sealing materials well known to those skilled in the art including but not limited to metallic or plastic foil, a plastic elastomer sheet, or a woven microscopically porous sheet and it can be attached to the connector hub 614 via adhesive, dip coating, over-molded, heat staking, ultrasonic welding, etc.

The connector body 514 interior is shown to contain the sealing plunger 526, a flexible accordion seal 534, and a compression spring 536. One end of the compression spring 536 is constrained by the inside 566 of the connector body 514 and the other end is pushing against the flexible accordion seal 534. The flexible accordion seal 534 in turn presses against part of the sealing plunger 526. In this manner, the compression spring 536, absent any other input, maintains the sealing plunger 526 position inside the UV transparent section 520 and isolates the lumen 530 of the tubular body 502 from the inside of the UV transparent section 520.

Referring now to FIGS. 15a-15c, the stop clips 628 have been removed as will be described in more detail later herein and the solution set catheter 600 has been completely engaged with the transfer set catheter 500 by further advancing the engaging threads 618 with the threads 518 on the inside of the end retainer 524. In this position the piercing member 554 on the sealing plunger 526 has broken through the leading membrane surface 620 and the leading membrane surface 620 has also pushed against the sealing plunger stop 558 and advanced the sealing plunger 526 out of the UV transparent section 520. Fluid can now pass from the transfer catheter lumen 530 passed the opened sealing luger 525, through the disinfected UV transparent section 520, passed the broken leading membrane surface 620 and into the solution set catheter lumen 680. A groove 574 is also provided in the sealing piston 526 to ensure that fluid can flow past the piston even when the piston is compressed against the flexible accordion seal 534.

Referring now to FIGS. 16a-b, 17a-c and 18a-c and alternate embodiment of the stop clips 728 are shown wherein these clips are separately molded or formed elements that are then adhered to the connector hub 614 by any number of ways including but not limited to, cyanoacrylate adhesive, 2-part epoxy adhesive, heat staking, ultrasonic welding, overmolding with a softer durometer polymer, etc. This embodiment has similar features to that described above in FIGS. 13a-b, 14a-c, and 15a-c. In addition, the stop clips 728 are comprised of projecting surface 722. The projecting surface 722 is configured to not be easily engaged by the user directly but to easily engage with a mating pocket 724 on the UV disinfecting unit as will be described more in detail later here within. The piercing member 554 of this embodiment is an integral feature in the sealing plunger 526 rather than an added element as was described in the embodiment shown in FIGS. 13b, 14c, and 15b-c.

Referring now to FIGS. 19a-c, 20a-c and 21a-b and alternate embodiment of the stop clips 828 are shown wherein these clips are separately molded or formed elements that are then adhered to the connector hub 614 by any number of ways including but not limited to, cyanoacrylate adhesive, 2-part epoxy adhesive, heat staking, ultrasonic welding, overmolding with a softer durometer polymer, etc. This embodiment has similar features to that described above in FIGS. 13a-b, 14a-c, and 15a-c. In addition, the stop clips 828 are comprised of projecting surface 822. The projecting surface 822 is configured to not be easily engaged by the user directly but to easily engage with a mating slot 824 on the UV disinfecting unit as will be described more in detail later here within.

Referring now to FIGS. 22a-d, 23a-c and 24a-c and alternate embodiment of the stop clips 928 are shown wherein these clips are separately molded or formed elements that are then adhered to the connector hub 614 by press fitting them onto posts 920 that are extending from the sides of the connector hub 614. This embodiment has similar features to that described above in FIGS. 13a-b, 14a-c, and 15a-c. In addition, the stop clips 928 are comprised of projecting surface 722. The projecting surface 722 is configured to not be easily engaged by the user directly but to easily engage with a mating pocket 724 on the UV disinfecting unit as will be described more in detail later here within. In addition, these stop clips 928 have curved sides 926 that further enable the stop clips to be removed from the connector hub 614 when the connector hub is advanced completely against the face 525 of the end retainer 524 of the transfer catheter. Also the stop clips have a detent pocket 925 that engages the detent projection 523 on the face 525 in the partially connected position shown in FIGS. 23a-c. This detent helps to hold the transfer catheter and solution set catheter in position for the UV disinfecting step. The detent projection 523 engages the detent 521 on the connector hub 614 when the connection is in the fully engaged position shown in FIGS. 24a-c. This final detent helps to hold the connection together and reduce the likelihood of the connection being unintentionally separated.

Figure 27A:
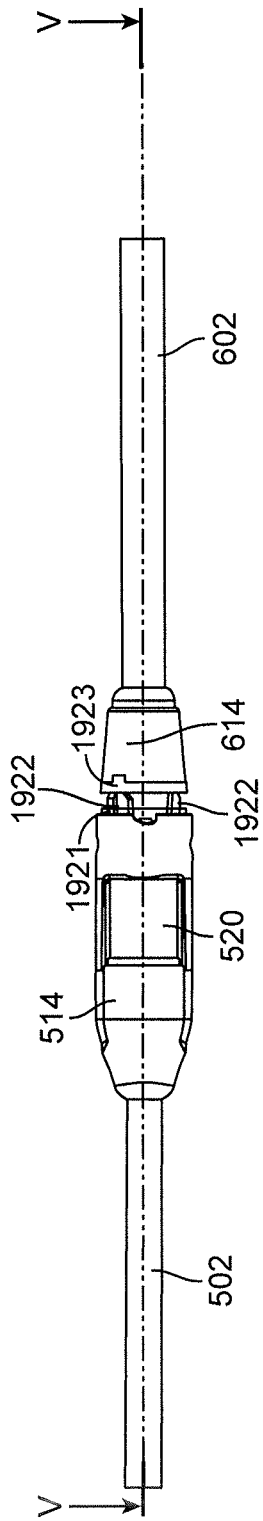
FIG. 27a is an illustration of a side view of embodiment of a catheter connection system.
Figure 27B:
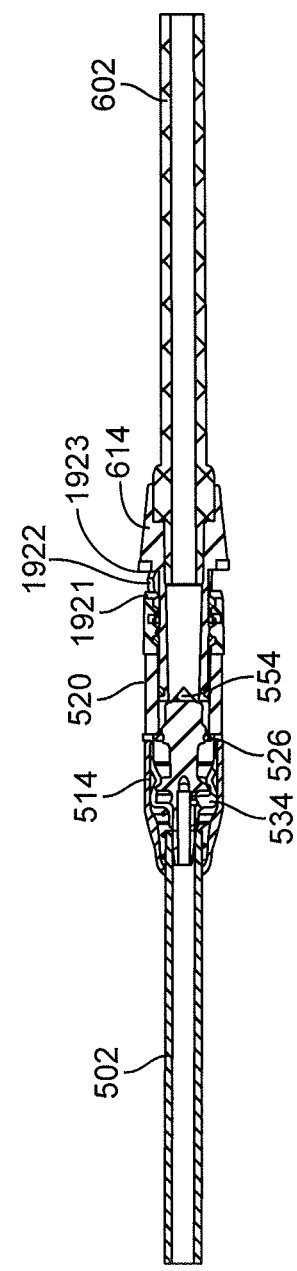
FIG. 27b is an illustration of a cross section view of an embodiment of a catheter connection system from FIG. 27a through line V-V.
Figure 28A:
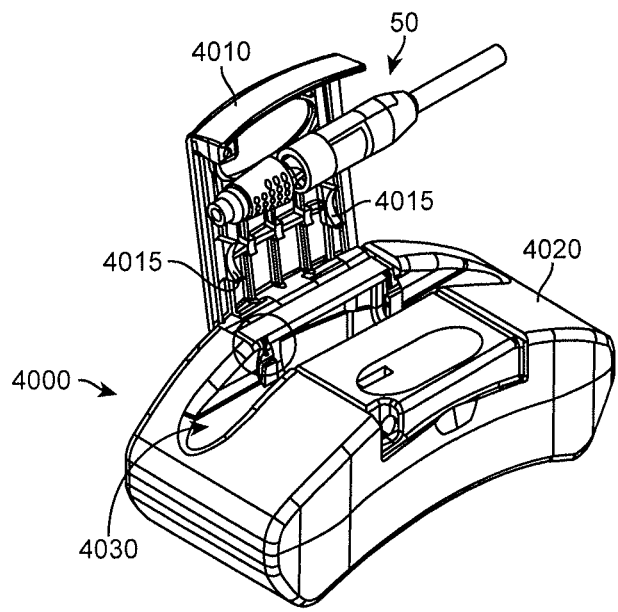
FIG. 28a is an illustration of a perspective view of a catheter connection system of FIG. 23a-23c and a UV disinfecting device.
Figure 28B:
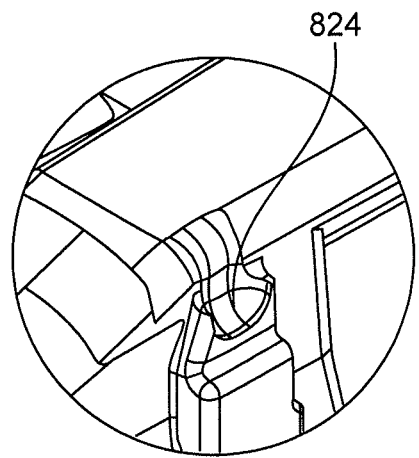
Figure 28C:
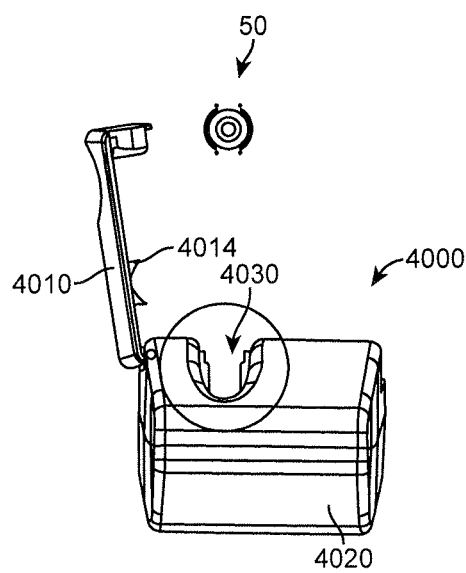
Figure 28D:
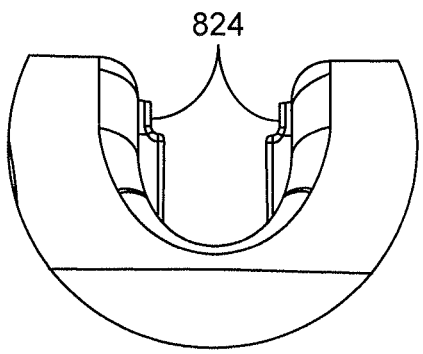
FIG. 28d is an illustration of a detail view of a UV disinfecting device from FIG. 28c.

Referring now to FIGS. 25a-b, 26a-b and 27a-b and alternate embodiment of the stop clip 1928 is shown wherein these clips are separately molded or formed elements that are then adhered to the connector hub 614 by inserting them over the hub barrel 1920. This embodiment has similar features to that described above in FIGS. 13a-b, 14a-c, and 15a-c. In addition, the stop clips 1928 are comprised of arms 1922 that extend between a front ring 1921 and a back ring 1923. The arms 1922 of the stop clip 1928 configured to not be easily buckled by the user directly but to easily engage with buckling projections on the UV disinfecting unit. Once engaged by the UV device unit the arms 1922 start to buckle at the thin portions 1927 near both rings 1921, 1923. The user can then complete the buckling by further advancing the solution set catheter 600 into the transfer set catheter 500 until the arms 1922 are completely collapsed against the rings 1921, 1923 as shown in FIGS. 27a-b.

Figure 29A:
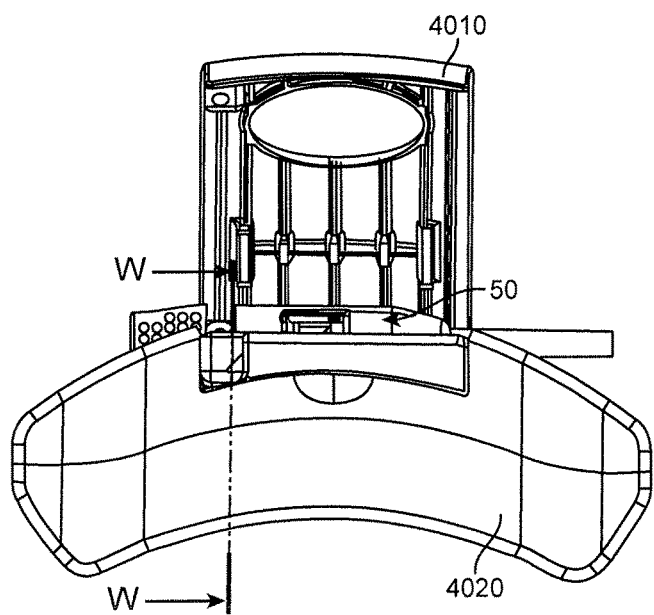
FIG. 29a is an illustration of a side view of a catheter connection system of FIG. 23a-23c and a UV disinfecting device.
Figure 29B:
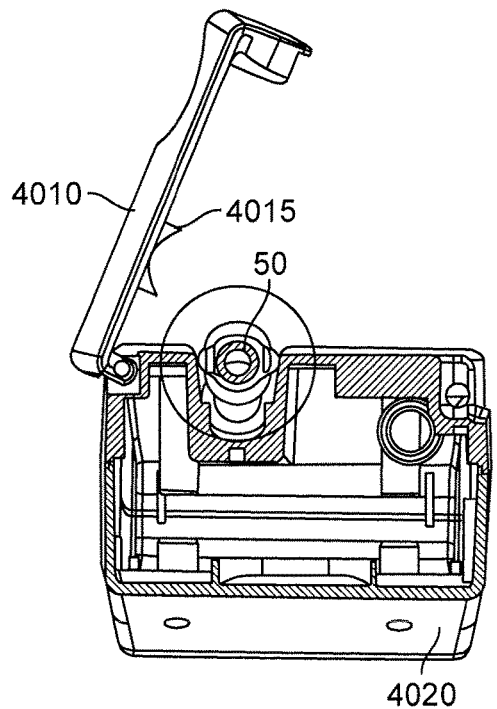
FIG. 29b is an illustration of a cross section view of a UV disinfecting device from FIG. 29a through line W-W.
Figure 29C:
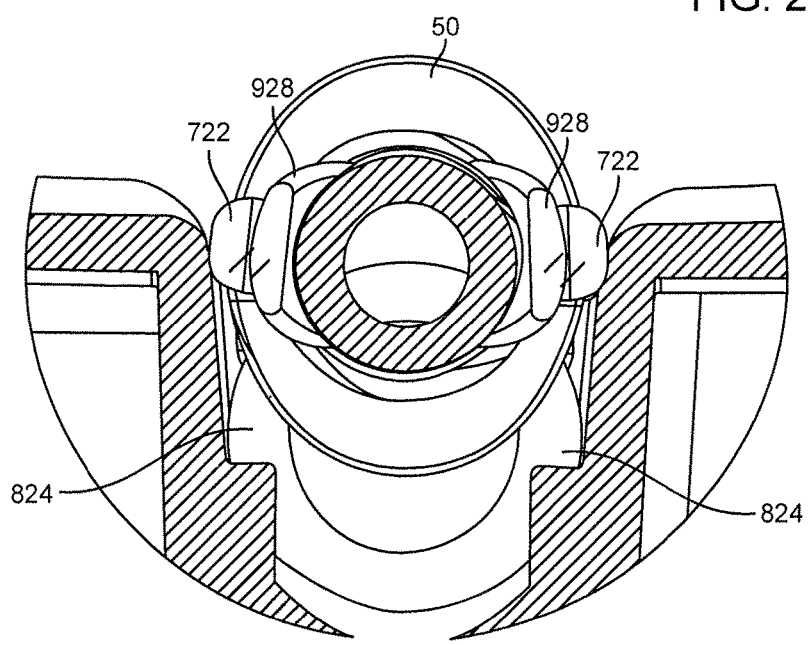
FIG. 29c is an illustration of a detail view of a catheter connection system and a UV disinfecting device from FIG. 29b.
Figure 30A:
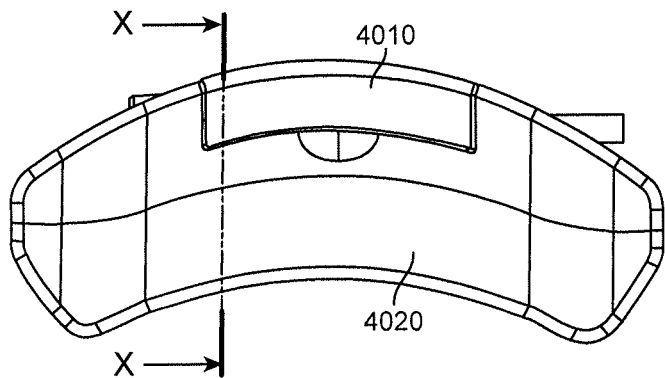
FIG. 30a is an illustration of a side view of a catheter connection system of FIG. 23a-23c and a UV disinfecting device.
Figure 30B:
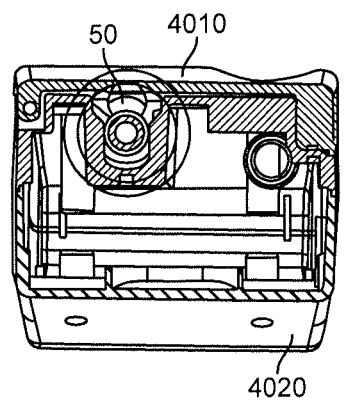
FIG. 30b is an illustration of a cross section view of a UV disinfecting device from FIG. 30a through line X-X.
Figure 30C:
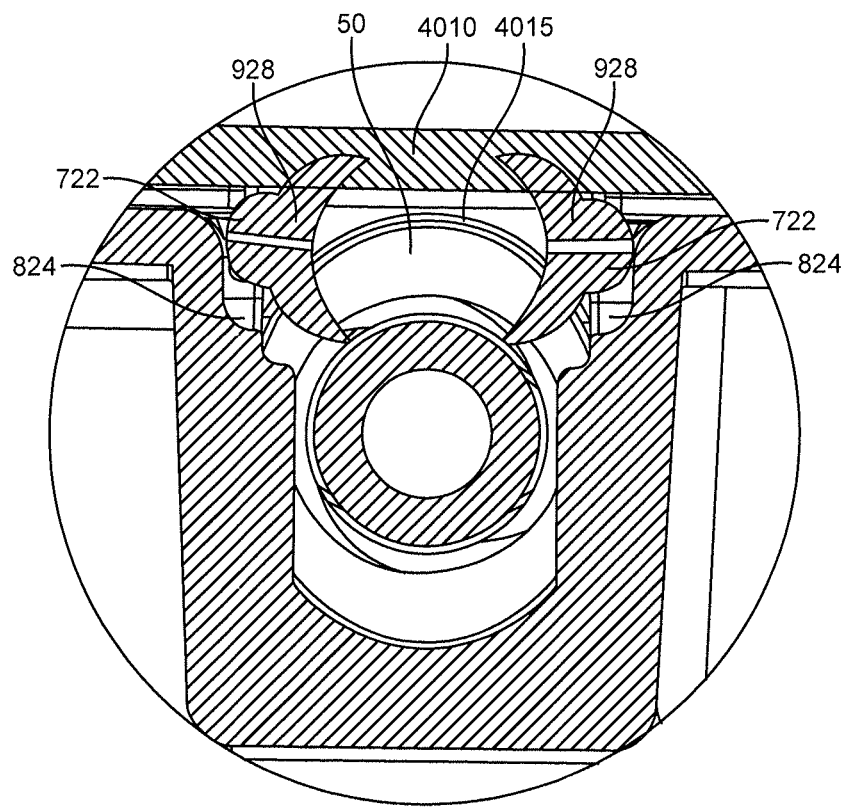
FIG. 30c is an illustration of a detail view of a catheter connection system and a UV disinfecting device from FIG. 30b.

Referring now to FIGS. 28a-28d, 29a-c, and 30a-c, a UV disinfecting device 4000 is shown which is configured for delivering UV energy to the catheter connection system 50 in order to disinfect the small controlled volume 528. The UV disinfecting device 4000 is comprised of a lid 4010 and a base 4020 and the base 4020 is configured with a channel 4030 for insertion of the catheter connection system 50. The lid 410 is comprised of one or more projections 4015 that are configured to guide the catheter connection system 50 into the channel 4030. The channel has one or more mating slots 824 that are configured to engage the projecting surfaces 722 of the stop clips 728, 928. When the catheter connection system 50 is placed into the channel 4030 the projecting surfaces 728 engage with the mating surfaces 824 preventing full insertion into the channel 4030 as shown in FIGS. 29a-c. When the lid 4010 is closed as shown in FIGS. 30a-c the projections 4015 force the catheter connection system 50 completely in the channel 4030 and the mating surfaces 824 force the stop clips 728, 928 off of the connector hub 614. In this manner the UV device 4000 not only is useful in disinfecting the catheter connection system 50, but also is required to remove the stop clips 728, 928 so that the catheter connection system 50 can be fully engaged and a fluid exchange can occur.

Referring to FIGS. 31a-c, and alternate embodiment of the UV device is shown comprised of a lid 410 and a base 420. In this embodiment, the channel 4030 and the lid 4010 are comprised of mating slots 824 configured to engage projecting surfaces 822 on the stop clips 828. When the lid 4010 is closed the projections 4015 force the projecting surfaces 822 into the mating slots 824. When the lid 4010 is opened after the UV disinfection cycle the mating slots retain the projecting surfaces 822 and pull the stop clips 824 off of the connector hub 614.

Figure 32:
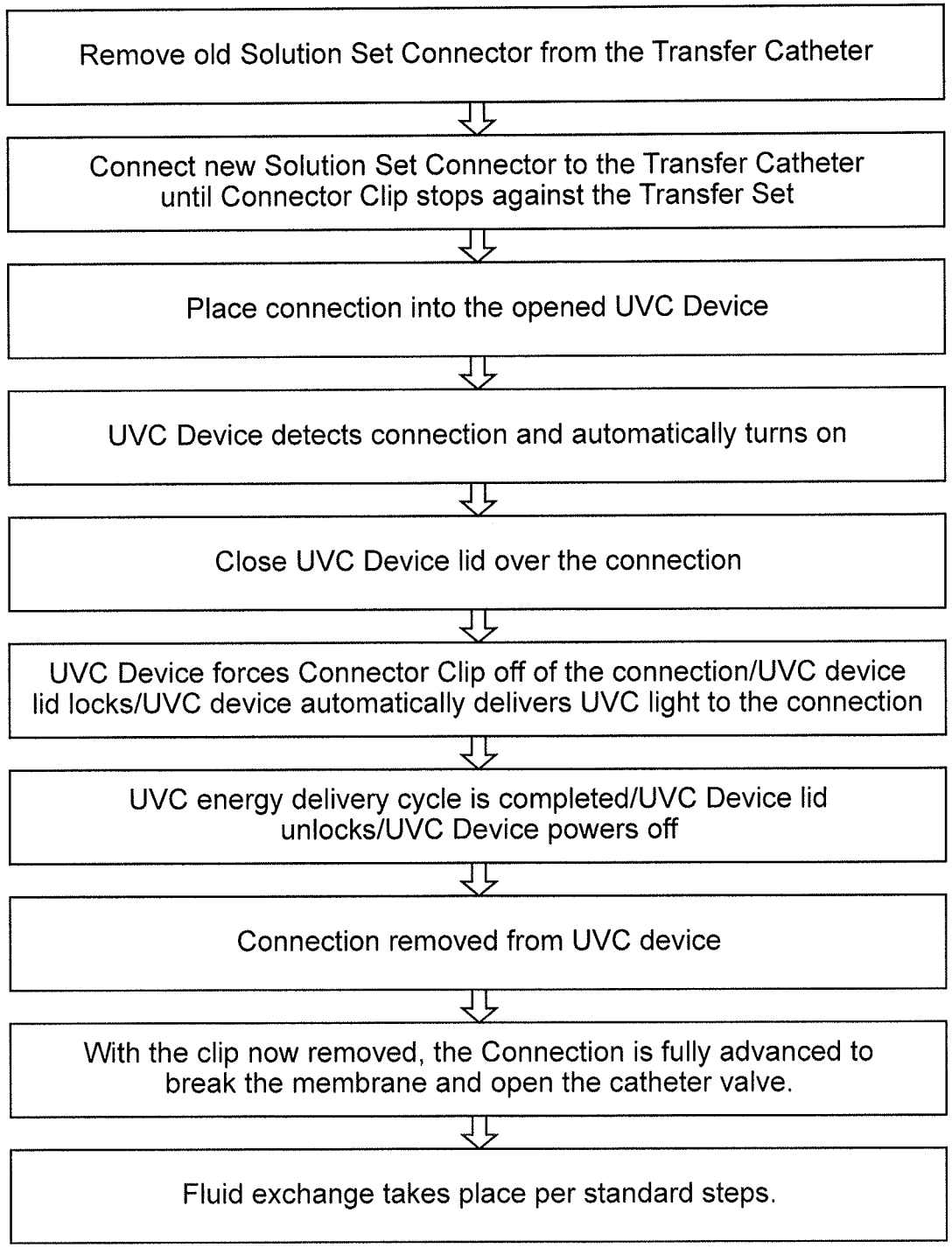
FIG. 32 illustrates an embodiment of a method for using a disinfection system during peritoneal dialysis.

Operation of the entire UV disinfecting device and catheter connection system can be achieved by following steps as shown in FIG. 32. Specifically, the sealed catheter connection system 50 from the previous exchange can be opened by removing the old solution set connector and discarding it. Then the new solution set catheter 600 can be engaged with the transfer set catheter 500 until the stop clip 628, 728, 828, 928, 1928 engages the face 525 of the end retainer 525. Then the catheter connection system 50 can be placed into the channel 4030 of the UV device 4000. The UV device 400 can automatically detect the catheter connection system 50 by any manner of methods know to those in the art including but not limited to magnetic sensors, optical sensors, MID chips, and the like. Once detected the UV disinfecting device 4000 can automatically power on without the need for the user to engage a power button or switch. This automatic power on is advantageous for 2 reasons, 1) it saves the user a step that takes some time and maybe forgotten, and 2) it prevents the UV device 4000 from being used on anything other than the intended catheter connection system 50. Next the user closes the lid 4010 which forces the catheter connection system 50 into the channel 4030 and either removes the stop clips 628,728,928, or engages them 828, 1928 for later removal 828 or reconfiguration 1928. The lid 4010 can be automatically locked to ensure that the catheter connection system 50 cannot be removed from the UV disinfecting device 4000 prior to the UV disinfecting cycle completion. The UV disinfecting cycle can also be automatically delivered once the lid 4010n is locked which not only says the user another step by can ensure that UV light is only safely delivered when the lid 4010 which covers the UV delivery area is locked. Once the UV disinfection cycle is completed, the lid 4010 can automatically unlock, the user can then open the lid 410 and remove the catheter connection system 50. Now the small controlled volume 528 is completely disinfected and the stop clips 628, 728, 828, 928, 1928 have been removed or reconfigured so that the solution set catheter 600 can now be completely engaged with the transfer set catheter 500 and the fluid exchange can occur within the sealed and disinfected system. This process prevents the user from fully engaging the transfer catheter 500 with the solution set catheter 600 without the use of the UV disinfecting device 4000 and thereby reduces the chance of the user introducing microbes into their body through the inner lumen 530 of the transfer set catheter 500.

It will be appreciated that while the disinfection system has been described in connection with peritoneal dialysis, the transfer catheter and/or solution set connectors can be used in numerous other applications, medical or otherwise. For example, features of the connectors/valves disclosed in PCT Application No. PCT/US15/25352, filed Apr. 10, 2015, and entitled "Connector Disinfection System"; U.S. application Ser. No. 14/731,110, filed Jun. 4, 2015, and entitled "Transfer Catheter for Ultraviolet Disinfection"; and PCT Application claiming the benefit of U.S. Provisional Application No. 62/360,922, and filed on Jul. 11, 2017, the disclosures of which are incorporated by reference herein in their entireties, can be used in the connector systems described herein.

Although the embodiments described herein contain particular combinations of the various elements of the current invention, it will be obvious to those skilled in the art that these elements can be combined in many other variations to provide the features needed without departing from the current invention. In the description herein UVC light was mention as a method of disinfection of microorganisms. Although the UVC wave length of approximately 260 nanometer wavelength is particularly effective in disinfection of microorganisms, longer UVB wavelengths can be used for disinfection without departing from the current invention. The elements of the current invention are depicted as generally cylindrical in shape as is typical of most catheter systems. However, any element, portion of the system, or the entire system can be in a non-cylindrical shape to achieve the desired function without departing from the current invention.

What is claimed is:

1. A catheter connection system, comprising:
a first connector comprising a UV transparent region at a first end of the first connector and a first seal proximal to the UV transparent region;
a second connector comprising a leading membrane surface and a second seal for sealing against the UV transparent region at a first end of the second connector, wherein the first end of the second connector is configured to mate with the first end of the first connector in a first disinfection position in which the first seal and the leading membrane surface are blocks between the first and second connectors and a second flow position in which the first seal is deflected and the leading membrane surface is ruptured to allow flow between the connectors;
a piercing member configured to pierce the leading membrane surface; and
a clip connected to at least one of the first connector and second connector, the clip configured to prevent movement from the disinfection position to the flow position, wherein the clip is configured to be removed or broken by interaction of the clip with a UV disinfection unit.

2. The system of claim 1, wherein the clip is configured to be broken by interaction with the UV disinfection unit.

3. The system of claim 1, wherein the clip is configured to be pushed off by interaction with the UV disinfection unit.

4. The system of claim 1, wherein the clip is configured to be pulled off by interaction with the UV disinfection unit.

5. The system of claim 1, wherein the clip is configured to be collapsed by interaction with the UV disinfection unit.

6. The system of claim 1, wherein the interaction comprises closing of a door of the UV disinfection unit.

7. The system of claim 1, wherein, in the disinfection position, a small volume disinfection zone is bounded by the leading membrane surface, and inner surface of the UV transparent region, the first seal, and the second seal.

8. The system of claim 1, wherein the UV transparent region comprises at least one of quartz glass, cyclic olefin copolymer, and polymethylpentene.

9. The system of claim 1, wherein a second end of the second connector is configured to connect to a tubular member through a sealed connector, the tubular member removable from the second connector while maintaining the seal at the second end of the second connector.

10. The system of claim 1, wherein the first connector is configured to connect to an indwelling catheter.

11. The system of claim 1, wherein the second connector is configured to connect to a solution set catheter.

12. The system of claim 1, wherein the second connector comprises the piercing member.

13. The system of claim 1, wherein the first connector comprises the piercing member.

14. The system of claim 1, further comprising a spring maintaining the first seal in a sealing position within the UV transparent region.

15. The system of claim 1, wherein the first seal comprises the piercing member.

* * * * *